United States Patent
Naganathan et al.

(10) Patent No.: US 9,771,347 B2
(45) Date of Patent: Sep. 26, 2017

(54) PROCESS FOR MAKING COMPOUNDS FOR USE IN THE TREATMENT OF CANCER

(71) Applicant: Exelixis, Inc., South San Francisco, CA (US)

(72) Inventors: Sriram Naganathan, San Jose, CA (US); Nathan Guz, Half Moon Bay, CA (US); Matthew Pfeiffer, Salt Lake City, UT (US); C. Gregory Sowell, San Francisco, CA (US); Tracy Bostick, St. John's Newfoundland (CA); Jason Yang, Pleasanton, CA (US); Amit Srivastava, Aiken, SC (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 14/684,826

(22) Filed: Apr. 13, 2015

(65) Prior Publication Data
US 2015/0210668 A1    Jul. 30, 2015

Related U.S. Application Data

(63) Continuation of application No. PCT/US2013/064866, filed on Oct. 14, 2013.

(60) Provisional application No. 61/713,104, filed on Oct. 12, 2012.

(51) Int. Cl.
*C07D 401/04*     (2006.01)
*C07D 498/04*     (2006.01)

(52) U.S. Cl.
CPC .......... *C07D 401/04* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 7,019,033 B2 * | 3/2006 | Barrett | C07C 215/68 514/235.8 |
| 7,803,839 B2 | 9/2010 | Aay et al. | |
| 7,915,250 B2 | 3/2011 | Aay et al. | |
| 7,956,191 B2 * | 6/2011 | Abel | C07D 213/79 546/310 |
| 7,999,006 B2 | 8/2011 | Lamb et al. | |
| 8,362,002 B2 | 1/2013 | Aay et al. | |
| 8,642,584 B2 | 2/2014 | Aftab et al. | |
| 2004/0039208 A1 * | 2/2004 | Chen | C07C 227/18 546/328 |
| 2010/0075947 A1 | 3/2010 | Aftab et al. | |
| 2014/0100215 A1 | 4/2014 | Aftab et al. | |
| 2014/0275527 A1 | 9/2014 | Aay et al. | |
| 2015/0141399 A1 | 5/2015 | Aay et al. | |

FOREIGN PATENT DOCUMENTS

| WO | WO 2007044515 A1 | 4/2007 |
|---|---|---|
| WO | WO 2008076415 A1 | 6/2008 |

OTHER PUBLICATIONS

International Search Report of PCT/US2013/064866, mailed Nov. 21, 2013.

\* cited by examiner

*Primary Examiner* — David K O'Dell
(74) *Attorney, Agent, or Firm* — Honigman Miller Schwartz and Cohn LLP; Heidi M. Berven; Jonathan P. O'Brien

(57) ABSTRACT

Disclosed herein is a process of making a compound of formula I

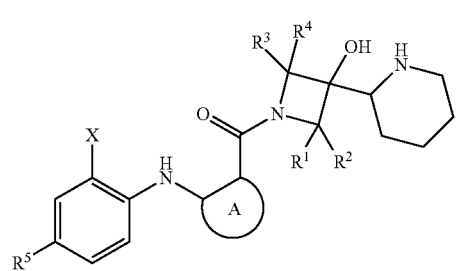

The compound of formula I is an inhibitor of MEK and thus can be used to treat cancer.

2 Claims, No Drawings

PROCESS FOR MAKING COMPOUNDS FOR USE IN THE TREATMENT OF CANCER

PRIORITY CLAIM

CROSS-REFERENCE TO RELATED APPLICATIONS

This application is a continuation of PCT Application No. PCT/US2013/064866, filed Oct. 14,2013, which claims priority to United States Provisional Application No. 61/713,104, filed Oct. 12, 2012. The entire contents of the aforementioned applications are incorporated by reference herein in their entirety.

FIELD OF THE INVENTION

The invention relates to a process for making certain compounds that inhibit MEK that are useful for the treatment of hyerproliferative disorders such as cancer. Such compounds are described in WO2007044515, the entire contents of which is incorporated by reference, and in ACS Med. Chem Lett., 2012, 3, 416-421.

BACKGROUND OF THE INVENTION

Like Ab1 kinase inhibition, MEK1 (MAPK/ERK Kinase) inhibition represents a promising strategy for treating cancers caused by aberrant ERK/MAPK pathway signaling (Solit et al., 2006; Wellbrock et al., 2004). The MEK-ERK signal transduction cascade is a conserved pathway which regulates cell growth, proliferation, differentiation, and apoptosis in response to growth factors, cytokines, and hormones. This pathway operates downstream of Ras which is often upregulated or mutated in human tumors. MEK is a critical effector of Ras function. The ERK/MAPK pathway is upregulated in 30% of all tumors, and oncogenic activating mutations in K-Ras and B-Raf have been identified in 22% and 18% of all cancers respectively (Allen et al., 2003; Bamford S, 2004; Davies et al., 2002; Malumbres and Barbacid, 2003). A large portion of human cancers, including 66% (B-Raf) of malignant melanomas, 60% (K-Ras) and 4% (B-Raf) of pancreatic cancers, 50% of colorectal cancers (colon, in particular, K-Ras: 30%, B-Raf: 15%), 20% (K-Ras) of lung cancers, 27% (B-Raf) papillary and anaplastic thyroid cancer, and 10-20% (B-Raf) of endometrioid ovarian cancers, harbor activating Ras and Raf mutations. Inhibition of the ERK pathway, and in particular inhibition of MEK kinase activity, results in anti-metastatic and anti-angiogenic effects largely due to a reduction of cell-cell contact and motility as well as downregulation of vascular endothelial growth factor (VEGF) expression. Furthermore, expression of dominant negative MEK or ERK reduced the transforming ability of mutant Ras as seen in cell culture and in primary and metastatic growth of human tumor xenografts in vivo. Therefore, the MEK-ERK signal transduction pathway is an appropriate pathway to target for therapeutic intervention and compounds that target MEK present considerable therapeutic potential.

Accordingly, there is an ongoing need for the identification of compounds that inhibit MEK for the treatment of cancer as well as processes for making such compounds.

SUMMARY OF THE INVENTION

Provided herein is a process for making compounds of formula I:

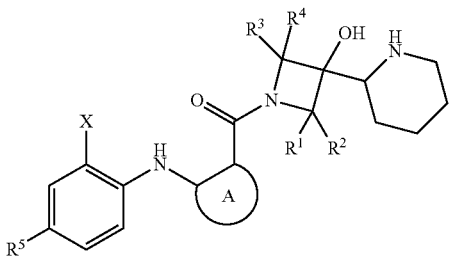

wherein:

Ring A is arylene or heteroarylene optionally substituted with one, two, three, or four groups selected from $R^6$, $R^7$, $R^8$, and $R^9$, each of which are independently selected from hydrogen, halo, $(C_1-C_8)$alkyl, halo$(C_1-C_8)$alkyl, hydroxy, $(C_1-C_6)$alkoxy, and halo$(C_1-C_6)$alkoxy;

X is alkyl, halo, halo$(C_1-C_8)$alkyl, or halo$(C_1-C_6)$alkoxy;

$R^1$, $R^2$, $R^3$, and $R^4$ are each independently hydrogen, $(C_1-C_8)$alkyl, or halo$(C_1-C_8)$alkyl;

$R^5$ is hydrogen, halo, or $(C_1-C_8)$alkyl;

comprising:

contacting a compound of formula $II_a$-1 with a compound of formula II-1 to provide a compound of formula I, wherein X and $R^5$ are as defined above, and wherein $R^{10}$ is F, Br, Cl, or —OSO$_2$—CF$_3$ and $R^{11}$ is H or a protecting group.

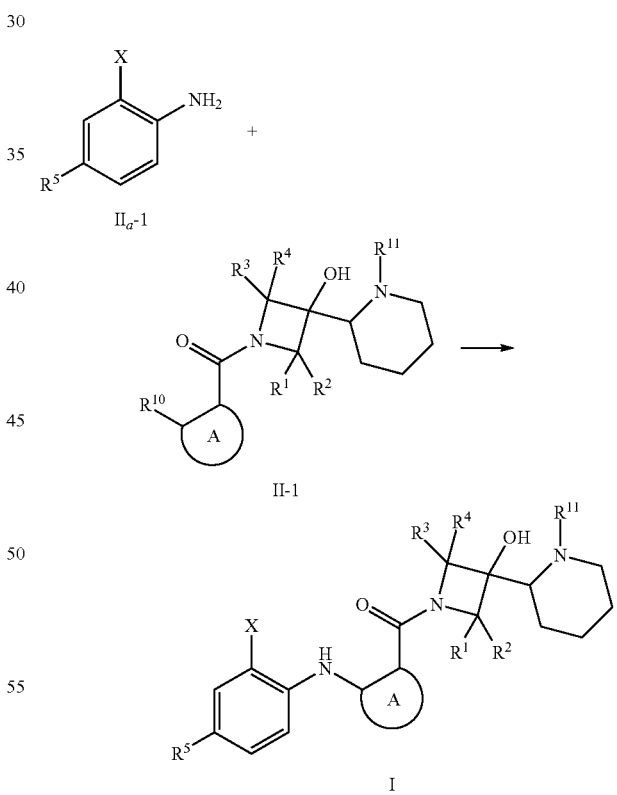

DETAILED DESCRIPTION OF THE INVENTION

Abbreviations and Definitions

The following abbreviations and terms have the indicated meanings throughout:

| Abbreviation | Meaning |
| --- | --- |
| Ac | Acetyl |
| Aq | Aqueous |
| Ar | Argon |
| Boc | Tert-butoxycarbonyl |
| Br | Broad |
| ° C. | Degrees Celsius |
| c- | Cyclo |
| calcd | Calculated |
| CBZ | CarboBenZoxy = benzyloxycarbonyl |
| d | Doublet |
| dd | Doublet of doublets |
| ddd | Doublet of doublets of doublets |
| dt | Doublet of triplets |
| DMF | N,N-Dimethylformamide |
| DMSO | Dimethyl sulfoxide |
| Dppf | 1,1'-bis(diphenylphosphano)ferrocene |
| EA | Elemental Analysis |
| EI | Electron Impact ionization |
| eq | Equivalent |
| Fmoc | Fluorenylmethyloxycarbonyl |
| g | Gram(s) |
| h or hr | Hour(s) |
| HPLC | High pressure liquid chromatography |
| $H_2$ | Hydrogen |
| L | Liter(s) |
| LiHMDS | Lithium bis(trimethylsilyl)azide |
| M | Molar or molarity |
| m | Multiplet |
| MHz | Megahertz (frequency) |
| Min | Minute(s) |
| mL | Milliliter(s) |
| Mp | Melting point |
| m/z | Mass to charge ratio |
| μL | Microliter(s) |
| Mol | Mole(s) |
| MS | Mass spectral analysis |
| $N_2$ | Nitrogen |
| N | Normal or normality |
| nM | Nanomolar |
| NMR | Nuclear magnetic resonance spectroscopy |
| Pd/C | Palladium on carbon |
| Q | Quartet |
| RT | Room temperature |
| s | Singlet |
| soln | Solution |
| S/C | Substrate/catalyst ratio |
| t or tr | Triplet |
| THF | Tetrahydrofuran |
| TLC | Thin layer chromatography |
| v/v | Volume to volume |

The symbol "—" means a single bond, "═" means a double bond.

When chemical structures are depicted or described, unless explicitly stated otherwise, all carbons are assumed to have hydrogen substitution to conform to a valence of four. For example, in the structure on the left-hand side of the schematic below, there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

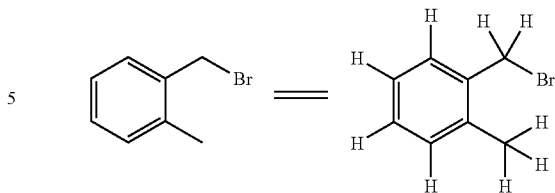

If a group "R" is depicted as "floating" on a ring system, as for example in the formula:

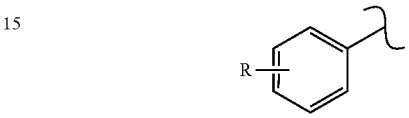

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

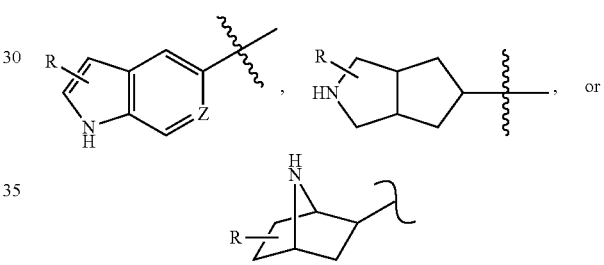

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "Z" equals ═CH—) from one of the ring atoms, so long as a stable structure is formed. In the example depicted, the "R" group may reside on either the 5-membered or the 6-membered ring of the fused ring system. When a group "R" is depicted as existing on a ring system containing saturated carbons, as for example in the formula:

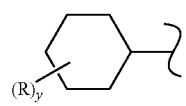

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group, there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

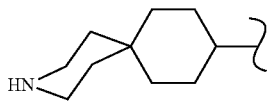

"Halogen" or "halo" refers to fluorine, chlorine, bromine, or iodine.

"Alkyl" refers to a branched or straight hydrocarbon chain of one to eight carbon atoms, such as methyl, ethyl, n-propyl, isopropyl, n-butyl, isobutyl, sec-butyl, t-butyl, pentyl, hexyl, and heptyl. $(C_1-C_6)$alkyl is preferred.

"Alkoxy" refers to a moiety of the formula —$OR^a$, wherein $R^a$ is an $(C_1-C_6)$alkyl moiety as defined herein. Examples of alkoxy moieties include, but are not limited to, methoxy, ethoxy, isopropoxy, and the like.

"Alkoxycarbonyl" refers to a group —C(O)—$R^b$ wherein $R^b$ is $(C_1-C_6)$alkoxy as defined herein.

"Aryl" means a monovalent six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

"Arylene" means a divalent six- to fourteen-membered, mono- or bi-carbocyclic ring, wherein the monocyclic ring is aromatic and at least one of the rings in the bicyclic ring is aromatic. Representative examples include phenylene, naphthylene, and indanylene, and the like.

"$(C_3-C_8)$Cycloalkyl" refers to a single saturated carbocyclic ring of three to eight ring carbons, such as cyclopropyl, cyclobutyl, cyclopentyl, and cyclohexyl. Cycloalkyl may optionally be substituted with one or more substituents, preferably one, two, or three substituents. Preferably, cycloalkyl substituent is selected from the group consisting of $(C_1-C_6)$alkyl, hydroxy, $(C_1-C_6)$alkoxy, halo$(C_1-C_6)$alkyl, halo$(C_1-C_6)$alkoxy, halo, amino, mono- and di$(C_1-C_6)$alkylamino, hetero$(C_1-C_6)$alkyl, acyl, aryl, and heteroaryl.

"Cycloalkyloxycarbonyl" means a group —C(O)—$OR^c$ wherein $R^c$ is $(C_3-C_6)$cycloalkyl as defined herein.

"Phenyloxycarbonyl" refers to a group —C(O)—Ophenyl.

"Heteroaryl" means a monocyclic, fused bicyclic, or fused tricyclic, monovalent radical of 5 to 14 ring atoms containing one or more, preferably one, two, three, or four ring heteroatoms independently selected from —O—, —S(O)$_n$— (n is 0, 1, or 2), —N—, —N($R^x$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. $R^x$ is hydrogen, alkyl, hydroxy, alkoxy, acyl, or alkylsulfonyl. Unless stated otherwise, the valency may be located on any atom of any ring of the heteroaryl group, valency rules permitting. In particular, when the point of valency is located on the nitrogen, $R^x$ is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzopyranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, or N-oxide or a protected derivative thereof.

"Heteroarylene" means a monocyclic, fused bicyclic, or fused tricyclic, divalent radical of 5 to 14 ring atoms containing one or more, preferably one, two, three, or four ring heteroatoms independently selected from —O—, —S(O)$_n$— (n is 0, 1, or 2), —N—, —N($R^{19}$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. $R^{19}$ is hydrogen, alkyl, or alkenyl. Unless stated otherwise, the valencies may be located on any atom of any ring of the heteroarylene group, valency rules permitting. In particular, when the point of valency is located on the nitrogen, $R^x$ is absent. More specifically, the term heteroaryl includes, but is not limited to, thien-diyl, benzo[d]isoxazol-diyl, benzo[d]isothiazol-diyl, 1H-indazol-diyl (optionally substituted at the N1 position with $R^{19}$), benzo[d]oxazol-diyl, benzo[d]thiazol-diyl, 1H-benzo[d]imidazol-diyl (optionally substituted at the N1 position with $R^{19}$), 1H-benzo[d][1,2,3]triazol-diyl (optionally substituted at the N1 position with $R^{19}$), imidazo[1,2-a]pyridin-diyl, cinnolin-diyl, quinolin-diyl, pyridin-diyl, 1-oxido-pyridin-diyl, [1,2,4]triazolo[4,3-a]pyridin-diyl, and 2,3-dihydroimidazo[1,2-a]pyridin-diyl, and the like.

"Heterogeneous transition metal hydrogenation catalyst" (hydrogenation catalyst) refers to a transition metal hydrogenation catalyst which acts in a different phase than the substrate. Especially the transition metal hydrogenation catalyst is in the solid phase. The "support" can be merely a surface on which the metal is spread to increase the surface area. The supports are porous materials with a high surface area, most commonly alumina or various kinds of carbon. Further examples of supports include, but are not limited to, silicon dioxide, titanium dioxide, calcium carbonate, barium sulfate, diatomaceous earth, and clay. The metal itself can also act as a support, if no other support is present. More specifically the term "heterogeneous transition metal hydrogenation catalyst" includes but is not limited to, a Raney catalyst, Pd/C, Pd(OH)$_2$/C, Pd(OAc)$_2$ polyurea microcapsules (NP Pd(0) Encat™ 30), Au/TiO$_2$, Rh/C, Ru/Al$_2$O$_3$, Ir/CaCO$_3$, and Pt/C, or a mixture thereof. NP Pd(0) Encat™ 30 is Palladium(0), microencapsulated in polyurea matrix, and is available from Sigma Aldrich as Product Number 653667. This catalyst is available as a 45 percent mixture of nanoparticles of palladium approximately 2 nm in size in water, typically containing 0.4 mmol/g Pd(0) (dry basis), where the unit weight includes the weight of water. See Ley, S. V. et. al. *Org Lett.* 2003 Nov. 27; 5(24):4665-8. In a particular embodiment, the "heterogeneous transition metal hydrogenation catalyst" is not pre-treated with sulphide.

"Strong base" refers to conjugate bases of weak acids with a pK$_a$>13 such as alkali metal salts of carbanion, alkoxides, amides, hydroxides, and hydrides, in particular the strong bases are lithium, sodium, potassium, rubidium, or cesium salts of carbanion, alkoxides, amides, hydroxides, and hydrides. More particularly strong base according to the invention refers to sodium, potassium, or lithium amide or phenyllithium, most particularly to butyllithium, t-butyllithium, lithium diisopropylamide, lithium bis(trimethylsilyl)amide, lithium diethylamide, potassium t-butoxide, lithium t-butoxide, sodium amide, and sodium hydride. Even more particularly, the strong base is butyllithium, lithium diisopropylamide, lithium bis(trimethylsilyl)amide, or lithium diethylamide.

"Strong acid" refers to an acid that dissociates completely in an aqueous solution with a pH≤2. The strong acids include, but are not limited to: sulphuric acid (H$_2$SO$_4$), hydrohalogenic acid (i.e. HX" wherein X" is I, Br, Cl or F), nitric acid (HNO$_3$), phosphoric acid (H$_3$PO$_4$), and combinations thereof. Particularly, the strong acid is H$_2$SO$_4$ or hydrohalogenic acid, wherein X" is Br or Cl. Most particularly, the strong acid is HCl. Particularly the concentration of HCl in water is in the range of 10% to 90%, more particularly 20% to 40%, most particularly 37%.

"Amino protecting groups" refers to an acid or base labile amino protecting groups, such as C$_1$-C$_6$alkoxycarbonyl, C$_3$-C$_6$cycloalkyloxycarbonyl, phenyloxycarbonyl, or toluenesulfonyl. In particular, examples of "amino protecting groups" include, but are not limited to, tert-butoxycarbonyl (Boc), benzyloxycarbonyl (Cbz), p-Toluenesulfonyl (Ts), and fluorenylmethyloxycarbonyl (FMoc). In particular, "amino protecting groups" refers to tert-butoxycarbonyl. (See Peter G. M. Wuts & Theodora W. Greene, Greene's Protective Groups in Organic Synthesis, 4$^{th}$ ed. (2006)).

Particularly, for the terms which definitions are given above are those specifically exemplified in the Examples.

"Yield" for each of the reactions described herein is expressed as a percentage of the theoretical yield.

Any one of the process steps or sequences disclosed and/or claimed herein can be performed under an inert gas atmosphere, more particularly under argon or nitrogen. In addition, the methods of the present invention may be carried out as semi-continuous or continuous processes, more preferably as continuous processes.

Moreover, many of the process steps and sequences that are described herein can be telescoped.

Embodiments of the Invention

In one aspect, the present invention provides a process for preparing a compound of formula I, comprising contacting a compound of formula II$_a$-1 with a compound of formula II-1, wherein X and R$^5$ are as defined above, and wherein R$^{10}$ is F, Cl, Br, I, or —OSO$_2$—CF$_3$ and the other variables are as previously defined.

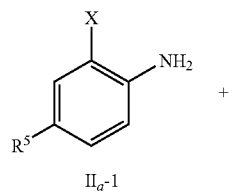

II$_a$-1

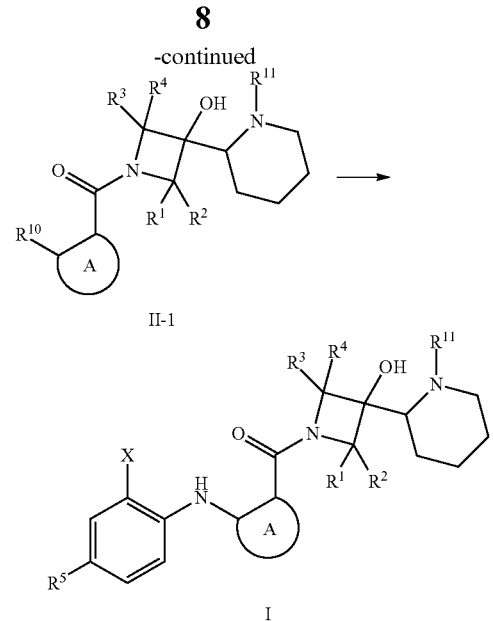

In one embodiment, X and R$^5$ in a compound of formula II$_a$-1 are each independently F, Cl, Br, or I. In another embodiment, X is F and R$^5$ is I.

In one embodiment, the compound of formula II-1 is the compound of formula II-2,

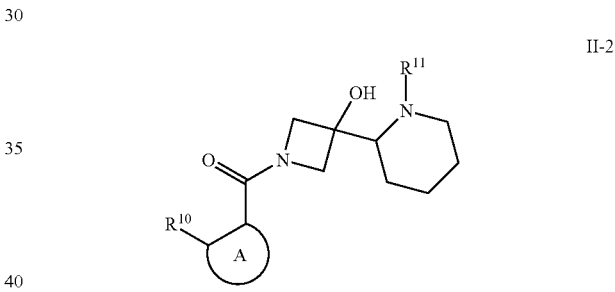

wherein R$^{11}$ is as H or a protecting group and Ring A is optionally substituted with one, two, three, or four groups selected from R$^6$, R$^7$, R$^8$, and R$^9$, each of which are independently selected from halo, (C$_1$-C$_8$)alkyl, halo(C$_1$-C$_8$)alkyl, (C$_1$-C$_6$)alkoxy, and halo(C$_1$-C$_6$)alkoxy.

In a particular embodiment of the present invention, Ring A is phenyl or pyridyl. More particularly, Ring A is phenyl substituted with R$^{12a}$ and R$^{12b}$ which are each independently F, Cl, Br, I, alkyl, haloalkyl, alkoxy, or haloalkoxy.

In another embodiment, the compound of formula II-1 is the compound of formula II-3,

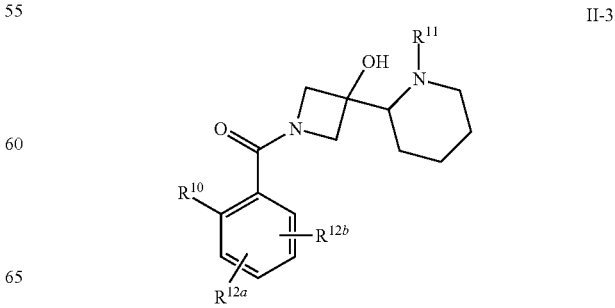

wherein R[11] is as defined previously and R[10] is F, Cl, Br, I, or OSO$_2$CF$_3$, and R[12a] and R[12b] are each independently F, Cl, Br, I, alkyl, haloalkyl, alkoxy, or haloalkoxy.

In one embodiment of the compound of formula II-1, II-2, or II-3, R[10] is F, Cl, Br, or I, and R[12a] and R[12b] are each independently F, Cl, Br, I, alkyl, haloalkyl, alkoxy, or haloalkoxy.

In another embodiment of the compound of formula II-1, II-2, or II-3, R[10] is F and R[12a] and R[12b] are each independently F, Cl, I, alkyl, or alkoxy.

In another embodiment the compound of formula II-1, II-2 or II-3, R[10] is F and R[12a] and R[12b] are each independently F, Cl, I, or alkyl.

In one embodiment, the present invention provides a process for preparing a compound of formula I', comprising contacting a compound of formula II$_a$ with a compound of formula II, the synthesis of which is described below.

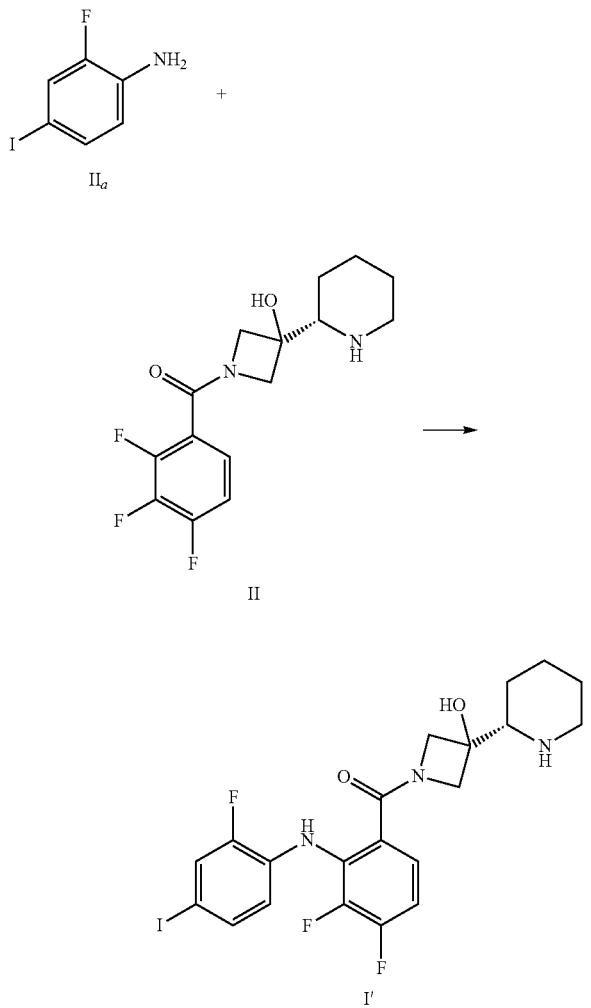

In another embodiment, the present invention provides a process for preparing a compound of formula I', comprising contacting a compound of formula II$_a$ with a compound of formula II in the presence of a strong base. In a particular embodiment, the strong base is selected from the group consisting of butyllithium, t-butyllithium, the lithium, sodium, or potassium salts of mono or bis substituted alkyl or aromatic amines, and silylalkyl or silylaromatic amines.

In a more particular embodiment, the strong base is selected from the group consisting of the lithium, sodium, or potassium salts of diisopropyl amine, bis(trimethylsilyl) amine, diethylamine, and dimethylamine.

In another embodiment, the strong base is selected from the group consisting of the lithium, sodium, and potassium salts of bis(trimethylsilyl)amine.

In another embodiment, the strong base is selected from the group consisting of lithium diisopropylamide, lithium bis(trimethylsilyl)amide, and lithium diethylamide. More particularly, the base is lithium bis(trimethylsilyl)amide.

The skilled artisan will understand that in these and other embodiments, the strong base can be obtained commercially or generated in situ using conventional methods.

The reaction of a compound of formula II with a compound of formula II$_a$ is typically performed in the presence of a solvent. Typically, the solvent is selected from the group consisting of a an ether-like solvent (e.g., tetrahydrofuran, diisopropyl ether, t-butylmethyl ether, dibutyl ether, dimethyl acetal, dioxane, or 2-methyl tetrahydrofuran (2-MeTHF)); an aromatic solvent (e.g., toluene or t-butylbenzene), an aliphatic hydrocarbon solvent (e.g., hexanes, heptanes, or pentane); a saturated alicyclic hydrocarbon solvent (e.g., cyclohexane or cyclopentane); and a polar aprotic solvent (e.g., dimethylformamide or dimethyl sulfoxide), or a mixture thereof. Preferred solvents include toluene and tetrahydrofuran. In a particular embodiment, the solvent is tetrahydrofuran.

The compound of formula II$_a$ is generally commercially available or is readily prepared using methods well known to the person skilled in the art. For example, the compound of formula II$_a$ is available from Sigma Aldrich as 2-fluoro-4-iodo-aniline (CAS Registry Number (CASRN) 29632-74-4).

In a typical procedure, a strong base such as lithium bis(trimethylsilyl)amide (LiHMDS) is added to mixture of a compound of formula II-1 such as a compound of formula II and 2-fluoro-4-iodo aniline in a suitable ether-like solvent such as THF. The reaction mixture is typically quenched with aqueous acid, typically aqueous sulphuric acid or hydrochloric acid, and then worked-up according to conventional methods to provide a compound of formula I such as a compound of formula I'.

In another embodiment, the present invention provides a process for preparing a compound of formula II, comprising deprotecting a compound of formula III.

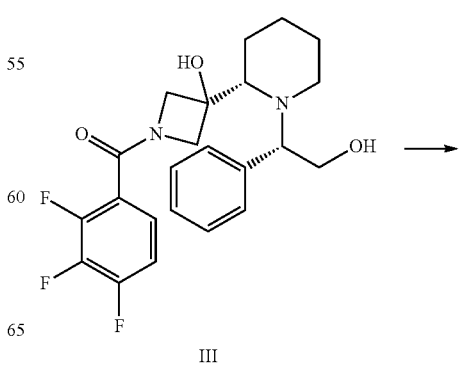

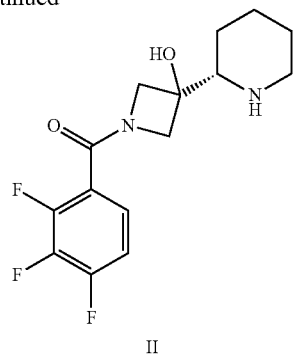

II

In one embodiment, the deprotection is accomplished in a suitable solvent using $H_2$ in the presence of a heterogeneous hydrogenation transition metal catalyst, or by treatment with chloroethyl chloroformate in the presence of MeCN or $Na/NH_3$. Preferably, the deprotection occurs by catalytic hydrogenolysis in the presence of a mineral acid such as HCl or an organic acid such as acetic acid or a mixture thereof, which accelerates the reaction. More particularly, the deprotection is accomplished via hydrogenolysis in the presence of a suitable solvent and in the presence of an acid such as hydrochloric acid or acetic acid or a mixture thereof. Most particularly, the deprotection is accomplished in the presence of HCl and acetic acid.

The heterogeneous hydrogenation transition metal catalyst can be any such catalyst known in the art. The catalyst is typically a heterogeneous transition metal catalyst which is typically selected from the group consisting of a Raney catalyst, Pd/C, Pd(OH)$_2$/C, Pd(OAc)$_2$ polyurea microcapsules (NP Pd(0) Encat™ 30), Au/TiO$_2$, Rh/C, Ru/Al$_2$O$_3$, Ir/CaCO$_3$, and Pt/C, or a mixture thereof. NP Pd(0) Encat™ 30 is Palladium(0), microencapsulated in polyurea matrix, and is available from Sigma Aldrich as Product Number 653667.

More particularly, the hydrogenation catalyst is selected from the group consisting of a Raney catalyst, Pd/C, Pd(OH)$_2$/C, Au/TiO$_2$, Rh/C, Ru/Al$_2$O$_3$, Ir/CaCO$_3$, and Pt/C, or a mixture thereof. More particularly, the hydrogenation catalyst is Pd/C, Pd(OH)$_2$/C, Au/TiO$_2$, Rh/C, Ra—Ni, or Pt/C. Most particularly, the hydrogenation catalyst is Pd/C or Ra—Ni. Palladium is used in catalytic amounts, e.g. 0.001 to 0.1 equivalents, preferably 0.01 to 0.1 equivalents, with respect to the compound of formula III.

The catalyst loading for the catalytic hydrogenolysis is typically 0.1 to 20 weight percent. More typically, the catalyst loading for the catalytic hydrogenolysis is typically 5 to 15 weight percent.

As indicated, the catalytic hydrogenolysis may be performed in the presence of a suitable solvent. Suitable solvents include alcohols (e.g. methanol or ethanol), ethers (e.g. tetrahydrofuran, diisopropyl ether, t-butylmethyl ether, dibutyl ether, dimethyl acetal, or dioxane), ester (e.g. ethyl acetate), aromatic hydrocarbons (e.g. toluene or t-butylbenzene), aliphatic hydrocarbons (e.g. hexanes, heptanes, or pentane), saturated alicyclic hydrocarbons (e.g. cyclohexane or cyclopentane), and aprotic polar solvents (e.g. dimethylformamide, or dimethyl sulfoxide) and a mineral or organic acid co-catalyst), used alone or as a mixture. More particularly, the solvent is toluene, ethyl acetate or tetrahydrofuran, or a mixture thereof, optionally in the presence of water. In one particular embodiment, the solvent is a mixture of tetrahydrofuran and ethyl acetate. In another particular embodiment, the solvent is toluene.

The catalytic hydrogenolysis is typically performed at a temperature between 0 and 50° C. More typically, the deprotection is performed at a temperature between 10 and 40° C. In a particular embodiment, the temperature is between 15 and 25° C.

Typically, the $H_2$ is added at a pressure of at least 0.1 bar, and more preferably at a pressure between 0.1 to 100 bar. More particularly, the $H_2$ is added at a pressure between 0.2 bar to 30 bar, and more particularly, the $H_2$ is added at a pressure of 1 to 10 bar. In a preferred embodiment, the $H_2$ is added at a pressure of approximately 2 bar.

In another embodiment, the present invention provides a process for preparing a compound of formula III, comprising contacting a compound of formula IV with a compound of formula IV$_a$.

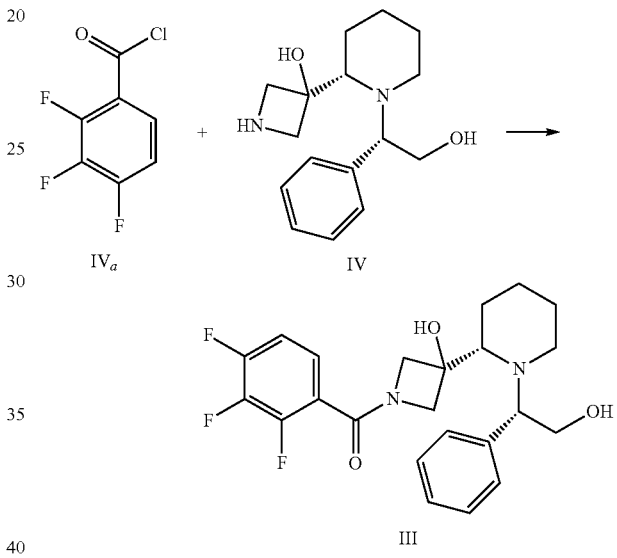

The compound of formula IV$_a$ (CASRN 157373-08-5) is generally available from commercial sources or is readily prepared by a skilled artisan. For instance, the compound of formula IV$_a$ can be prepared from the corresponding carboxylic acid (CASRN 61079-72-9) using thionyl chloride or oxalyl chloride or the like in the presence of a catalyst such as pyridine, dimethylformamide, triethyl amine, or diisopropylethyl amine.

In another embodiment, the present invention provides a process for preparing a compound of formula III, comprising contacting a compound of formula IV with a compound of formula IV$_a$ in the presence of a base.

In a particular embodiment of the invention, the base is an inorganic base, which is preferably an alkali or alkali earth metal hydroxide, phosphate, or carbonate. More particularly, the inorganic base is selected from the group consisting of LiOH, NaOH, KOH, CsOH, NH$_4$OH, RbOH, Mg(OH)$_2$, Ca(OH)$_2$, Ba(OH)$_2$, Li$_2$CO$_3$, Na$_2$CO$_3$, K$_2$CO$_3$, Cs$_2$CO$_3$, (NH$_4$)$_2$CO$_3$, and K$_3$PO$_4$. In a particular embodiment, the base is K$_3$PO$_4$, K$_2$CO$_3$, or KOH. In a more particular embodiment, the base is K$_3$PO$_4$, K$_2$CO$_3$, or KOH. The base is typically used as a mixture in water.

In one embodiment, the reaction is accomplished in a suitable solvent in the presence of the base. In one embodiment, the solvent is selected from the group consisting of an ether (e.g. tetrahydrofuran, diisopropyl ether, t-butylmethyl ether, dibutyl ether, dimethyl acetal, or dioxane, 2-MeTHF); an alcohol such as methanol or ethanol or the like; toluene; or a mixture thereof. In one particular embodiment, the solvent is toluene. In another particular embodiment, the solvent is a mixture of tetrahydrofuran and water. The reaction is typically performed at a temperature of approximately 10 to 20° C.

In another embodiment, the present invention provides a process for preparing a compound of formula IV$_a$, comprising reacting a compound of formula IV$_b$ with oxalyl chloride, thionyl chloride, or the like, in the presence of a catalyst such as pyridine, dimethylformamide, triethyl amine, or diisopropylethyl amine.

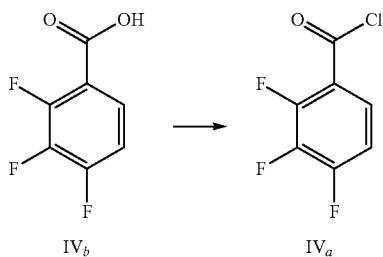 [SMILES: O=C(O)c1ccc(F)c(F)c1F ; O=C(Cl)c1ccc(F)c(F)c1F]

IV$_b$          IV$_a$

In a particular embodiment, the conversion of compound IV$_b$ to IV$_a$ is carried out in the presence of pyridine or dimethylformamide, particularly in the presence of trace amount of pyridine, more particularly wherein between about 0.001 and 0.02 eq of pyridine is being used, most particularly wherein about 0.005 eq of pyridine is being used.

In another embodiment, the present invention provides a process for preparing a compound of formula IV, comprising deprotecting a compound of formula V,

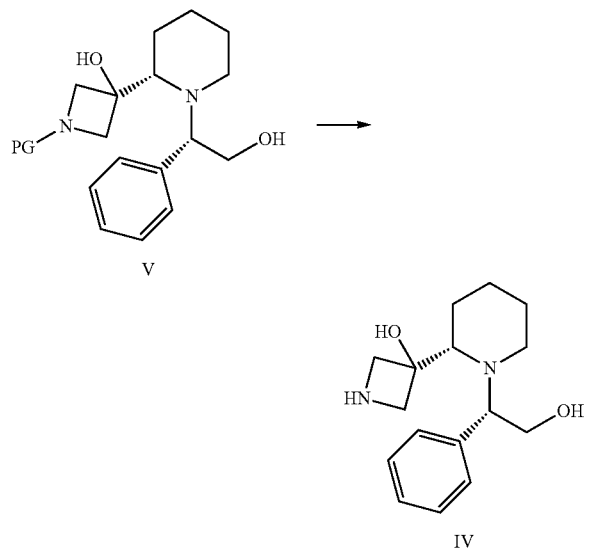

wherein PG is an amino protecting group. In one embodiment, the amino protecting group is an FMoc, CBz, or BOC protecting group. In a particular embodiment, the amino protecting group is a BOC protecting group.

The deprotection of a compound of formula V may be performed in the presence of a solvent, such as an alcohol (e.g. methanol or ethanol), an ether-like solvent (e.g. tetrahydrofuran, diisopropyl ether, t-butylmethyl ether, dibutyl ether, dimethyl acetal, or dioxane), ester-like solvent (e.g. ethyl acetate), aromatic solvent (e.g. toluene or t-butylbenzene), an aliphatic hydrocarbon solvent (e.g. hexanes, heptanes, or pentane), a saturated alicyclic hydrocarbon solvent (e.g. cyclohexane or cyclopentane), an aprotic polar solvents (e.g. dimethylformamide), or dimethyl sulfoxide and a mineral or organic co-catalyst, preferably in the presence of methanol, ethanol, isopropanol, tert-butanol, tetrahydrofuran, 2-methyltetrahydrofuran, toluene, or dimethylformamide and hydrochloric acid or acetic acid.

In a particular embodiment, the deprotection is carried out in a solvent in the presence of a strong mineral or organic acid, particularly trifluoroacetic acid, methansulfonic acid, p-toleunensulfonic acid, Lewis acids, particularly trialkylsilyl iodides, trimethylsilyl halides, boron trifuoride diethyl etherate, zinc halides, tin halides, or an inorganic acid. More particularly the acid is sulfuric acid, HBr, or HCl. Common conditions include HCl/dioxane, trifluoroacetic acid/methylene chloride. In one embodiment the deprotection is carried out in a heterogeneous mixture containing aqueous HCl and toluene.

In another embodiment, the present invention provides a process for preparing a compound of formula V wherein PG is an amino protecting group, comprising reducing a compound of formula VI.

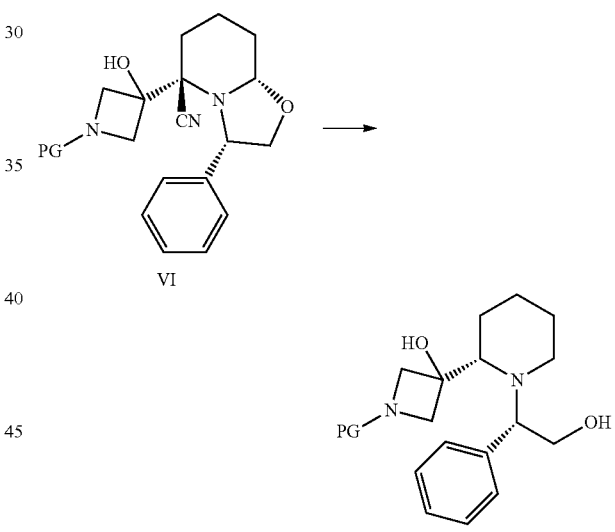

In one embodiment, the reaction occurs in the presence of a reducing agent. The reducing agent can be selected from the group consisting of borohydrides. In particular, the reducing agent is selected from the group consisting of NaBH$_4$, NaBH(OAc)$_3$, and NaBH$_3$CN. More preferably, the reducing agent is NaBH$_3$CN or NaBH$_4$ and LiCN, NaCN, or KCN under conditions used in typical reductive amination procedures. A typical reductive amination procedure involves combining an amine and a carbonyl compound in the presence of a complex metal hydride such as NaBH$_4$, LiBH$_4$, NaBH$_3$CN, Zn(BH$_4$)$_2$, sodium triacetoxyborohydride, or borane/pyridine under mild acidic conditions, conveniently at a pH of 1-5, which promotes formation of the intermediate iminium salt which is then reduced by the metal hydride. More preferably, the reducing agent is NaBH$_3$CN.

The preparation of a compound of formula V may be performed in the presence of a solvent, such as an alcohol solvent (e.g. methanol or ethanol), an ether-like solvent (e.g. tetrahydrofuran, diisopropyl ether, t-butylmethyl ether, dibutyl ether, dimethyl acetal, or dioxane), ester-like solvent (e.g. ethyl acetate), aromatic solvent (e.g. toluene or t-butylbenzene), an aliphatic hydrocarbon solvent (e.g. hexanes, heptanes, or pentane), a saturated alicyclic hydrocarbon solvent (e.g. cyclohexane or cyclopentane), an aprotic polar solvents (e.g. dimethylformamide), or dimethyl sulfoxide and a mineral or organic co-catalyst, preferably in the presence of methanol, ethanol, isopropanol, tert-butanol, tetrahydrofuran, 2-methyltetrahydrofuran, toluene, or dimethylformamide.

In another embodiment, the present invention provides a process for preparing a compound of formula VI comprising reacting a compound of formula VII (CASRN 106565-71-3) with a compound of formula VII$_a$,

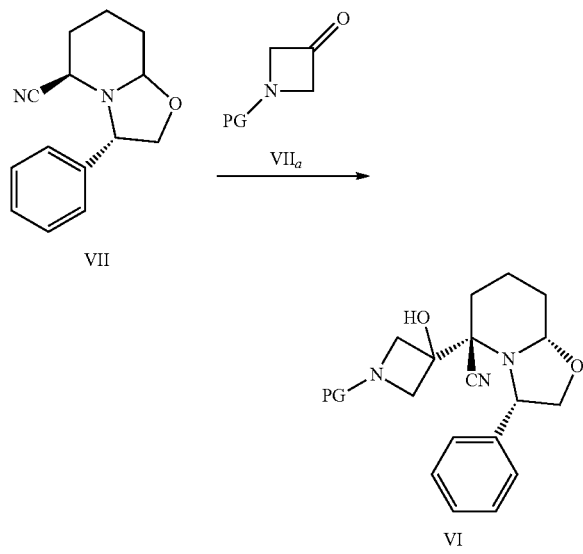

wherein PG is an amino protecting group such as Fmoc, Cbz, or Boc or the like. The compound of formula VII$_a$ is generally available from commercial sources or is readily prepared using methods well known to the person skilled in the art. (See, for example, Rice, K. et al. Med. Chem. Lett. 2012, 3, 416, and Podlech, J. and Seebach, D. Helv. Chim. Acta 1995, 1238.) For example, the compound of formula VII$_a$ wherein PG is Boc is commercially available from Sigma Aldrich as 1-Boc-azetidinone (tert-butyl 3-oxo-1-azetidinecarboxylate, CASRN 398489-26-4). Similarly, the compound of formula VII is generally available from commercial sources or is readily prepared using methods well known to the person skilled in the art. (See, for example, N. R. Guz et al., Org. Proc. Res. Develop. 2010 14(6):1476). For example, the compound of formula VII is commercially available, from Sigma Aldrich, as (3S,5R,8aS)-3-phenyl-hexahydro-oxazolo[3,2-a]pyridine-carbonitrile (CAS Reg. No. 106565-71-3).

In one embodiment, the reaction is accomplished in a suitable solvent in the presence of a base. In one embodiment, the solvent is a polar aprotic solvent selected from ethers such as tetrahydrofuran, diisopropyl ether, t-butylmethyl ether, dibutyl ether, dimethyl acetal, dioxane, or 2-MeTHF or mixtures thereof, used alone or in combination with a polar aprotic solvent such as 1,3-Dimethyl-3,4,5,6-tetrahydro-2(1H)-pyrimidinone (DMPU). In a particular embodiment, the solvent is THF used in combination with DMPU.

In this and other embodiments, the base is an amine base such as the lithium, sodium, or potassium salts of mono or bis substituted alkyl or aromatic amines, and silylalkyl or silylaromatic amines. In a particular embodiment, the strong base is selected from the group consisting of the lithium, sodium, or potassium salts of diisopropyl amine, bis(trimethylsilyl)amine, diethylamine, and dimethylamine. In another embodiment, the strong base is selected from the group consisting of the lithium, sodium, and potassium salts of bis(trimethylsilyl)amine. More particularly, the strong base is selected from the group consisting of lithium diisopropylamide, lithium bis(trimethylsilyl)amide, and lithium diethylamide. More particularly, the base is lithium diisopropylamide.

The reaction is typically performed at low temperature. In one embodiment, the reaction temperature is about 0 to −80° C. In another embodiment, the reaction temperature is about −20 to −80° C. In a more preferable embodiment, the reaction temperature is about −50 to −80° C. In another preferable embodiment, the reaction temperature is about −70 to −80° C.

In another embodiment, the present invention provides a process for preparing a compound of formula V, comprising the following steps:

1) reacting a compound of formula VII with a compound of formula VII$_a$ as previously described to provide a compound of formula VI;

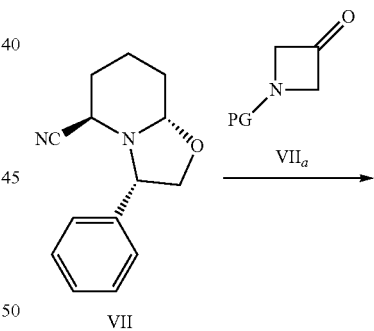

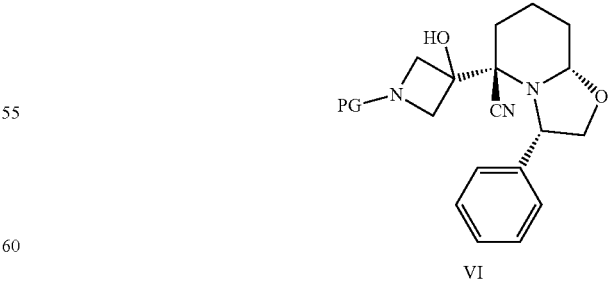

and 2) reducing a compound of formula VI with a reducing agent as previously described to provide a compound of formula V.

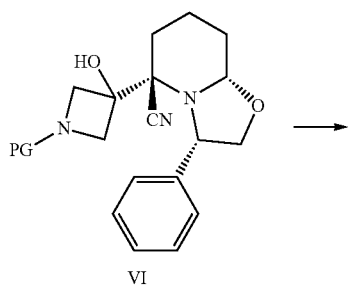

VI

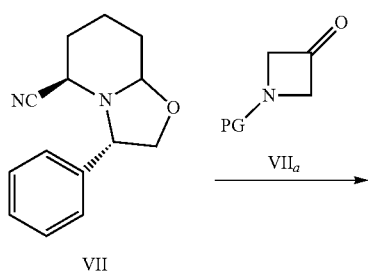

V

In one embodiment, steps 1 to 2 steps can be telescoped.

In another embodiment, the present invention provides a process for the preparation of the compound of formula IV, which comprises the following steps:

1) reacting a compound of formula VII with a compound of formula VII$_a$ as previously described to provide a compound of formula VI;

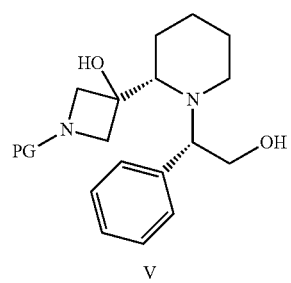

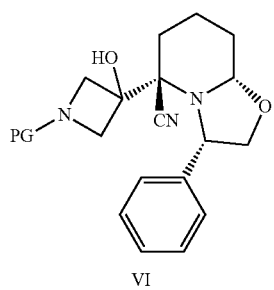

VI 2) reducing a compound of formula VI with a reducing agent as previously described to provide a compound of formula V;

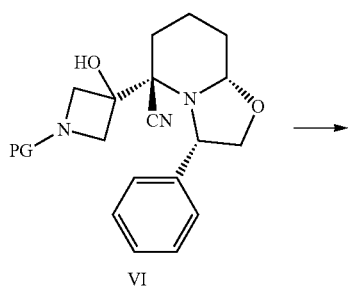

VI

-continued

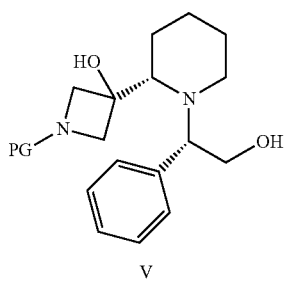

V and 3) deprotecting the azetidinyl ring of a compound of formula V as previously described to provide a compound of formula IV.

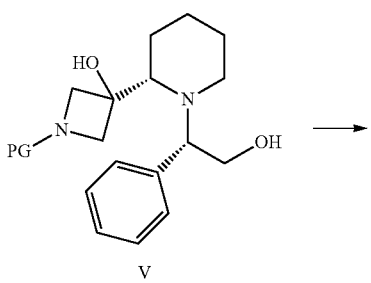

V

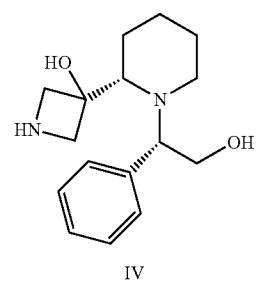

IV

In particular, any combination of steps 1 to 3 or all steps can be telescoped. More particularly steps 2 and 3 are telescoped.

In another embodiment, the present invention provides a process for the preparation of the compound of formula III, which comprises the following steps:

1) reacting a compound of formula VII with a compound of formula VII$_a$ as previously described to provide a compound of formula VI;

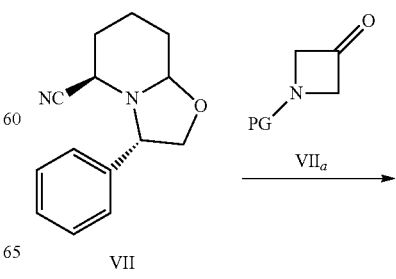

VII

-continued

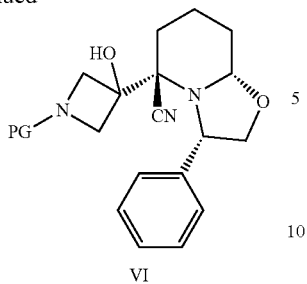

VI 2) reducing a compound of formula VI with a reducing agent as previously described to provide a compound of formula V;

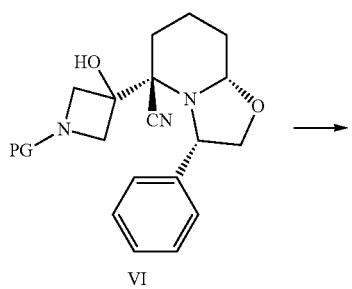

VI

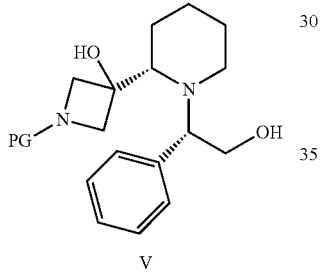

V 3) deprotecting the azetidinyl ring of a compound of formula V as previously described to provide a compound of formula IV;

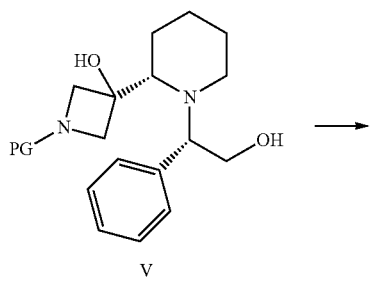

V

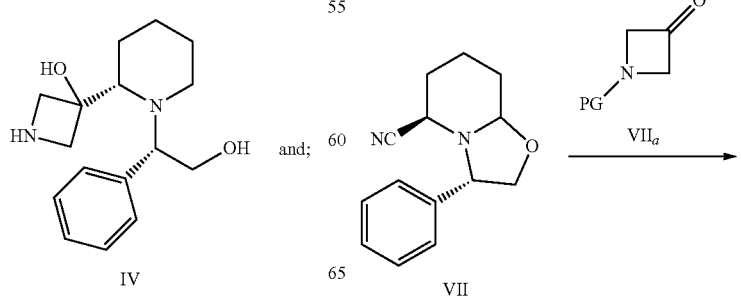

IV 4) reacting a compound of formula IV with a compound of formula IV$_a$, as previously described to provide a compound of formula III.

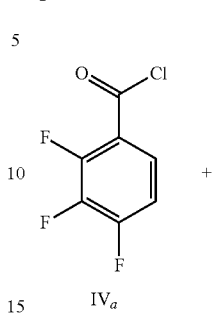

IV$_a$

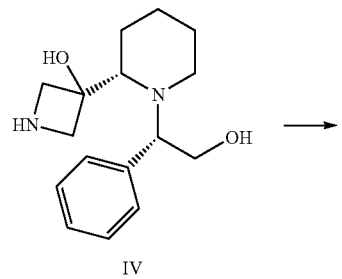

IV

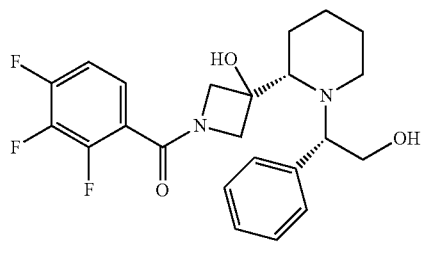

III

In particular, any combination of steps 1 to 4 or all steps can be telescoped. More particularly steps 2 to 4 are telescoped.

In another embodiment, the present invention provides a process for the preparation of the compound of formula II, which comprises the following steps:

1) reacting a compound of formula VII with a compound of formula VII$_a$ as previously described;

VII

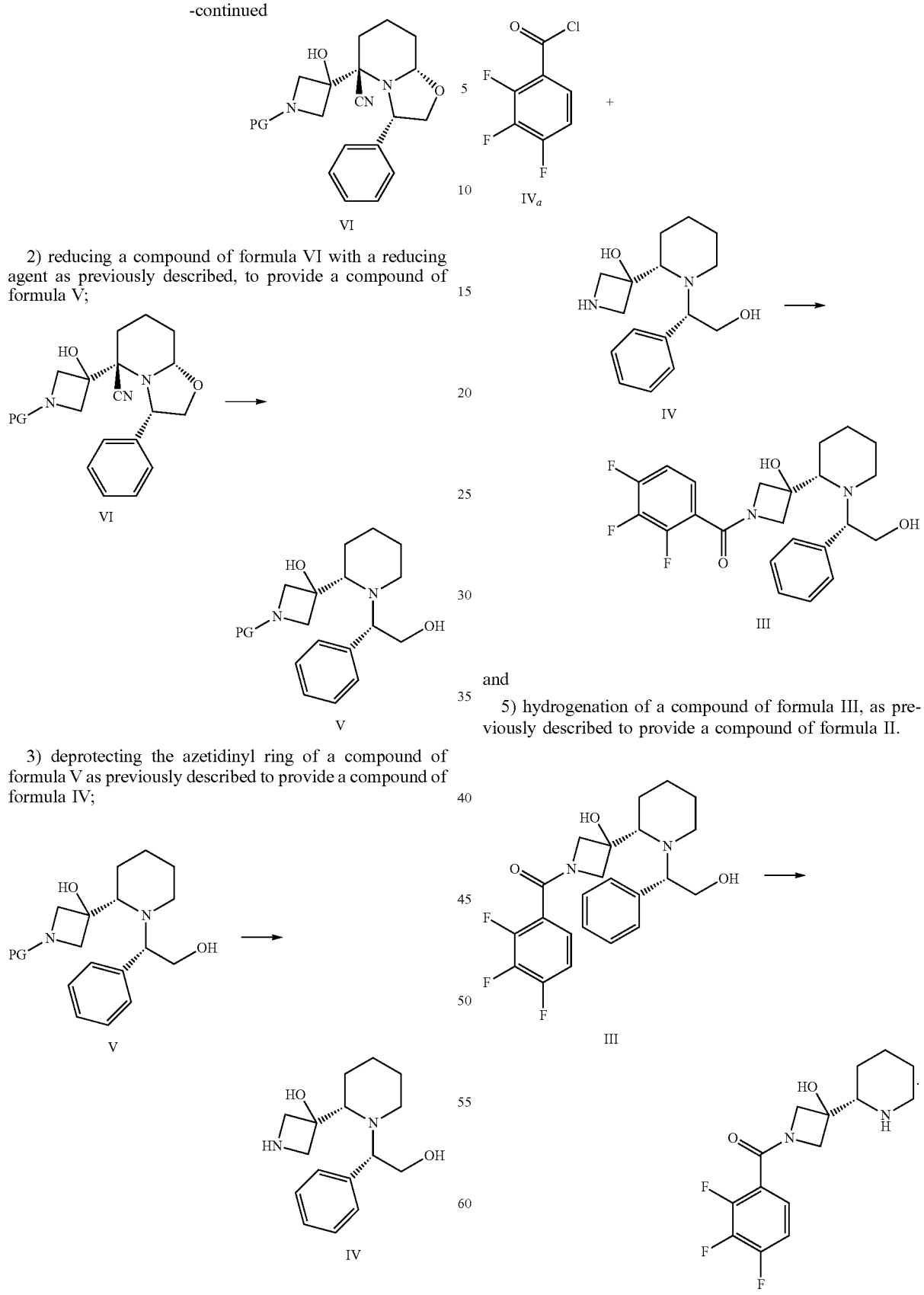

Any combination of steps 1 to 5 or all steps can be telescoped. More particularly steps 2 to 5 are telescoped.

In another embodiment, the present invention provides a process for the preparation of a compound of formula I', which comprises the following steps:

1) reacting a compound of formula VII with a compound of formula VII$_a$ as previously described to provide a compound of formula VI;

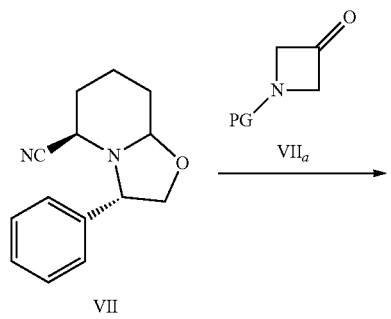

VII

VII$_a$

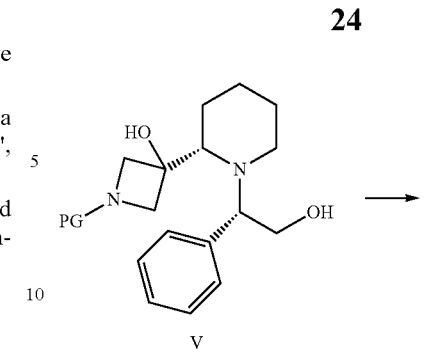

V 2) reducing a compound of formula VI with a reducing agent as previously described to provide a compound of formula V;

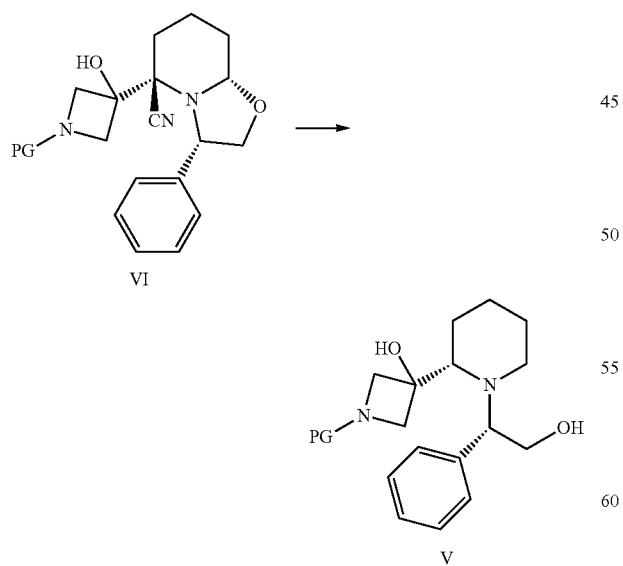

VI

V 3) deprotecting the azetidinyl ring of a compound of formula V as previously described to provide a compound of formula IV;

IV 4) reacting a compound of formula IV with a compound of formula IV$_a$ as previously described to provide a compound of formula III;

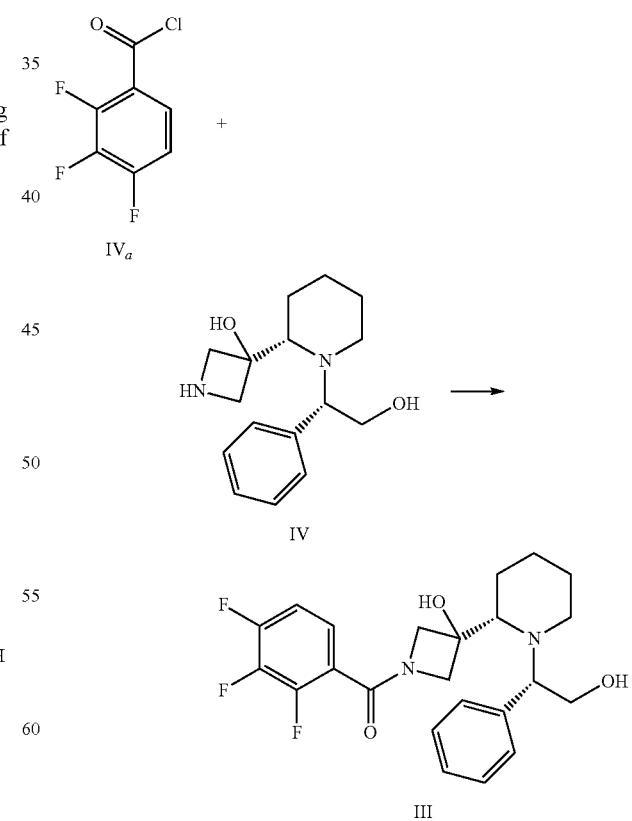

IV$_a$

IV

III 5) hydrogenation of a compound of formula III as previously described to provide a compound of formula II;

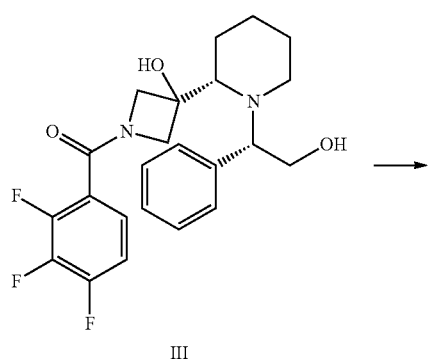

III

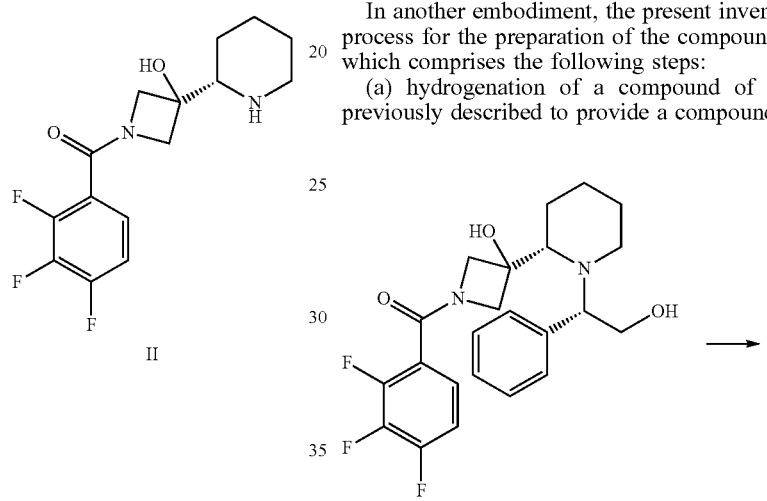

II and 6) reacting a compound of formula II with a compound of formula II$_a$ as previously described to provide a compound of formula I'.

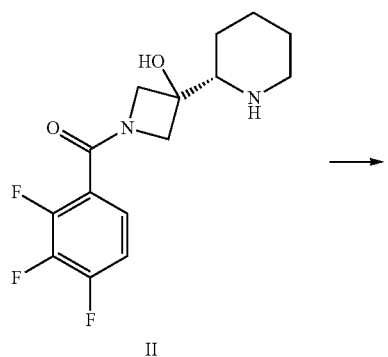

II

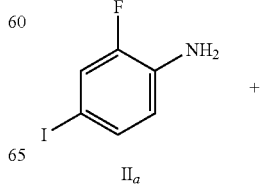

II$_a$

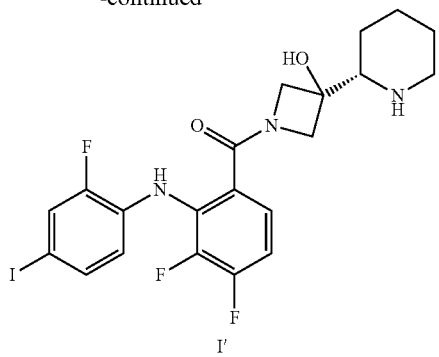

I'

In particular, any combination of steps 1 to 6 or all steps can be telescoped. More particularly, steps 2 to 5 are telescoped.

In another embodiment, the present invention provides a process for the preparation of the compound of formula I', which comprises the following steps:

(a) hydrogenation of a compound of formula III as previously described to provide a compound of formula II;

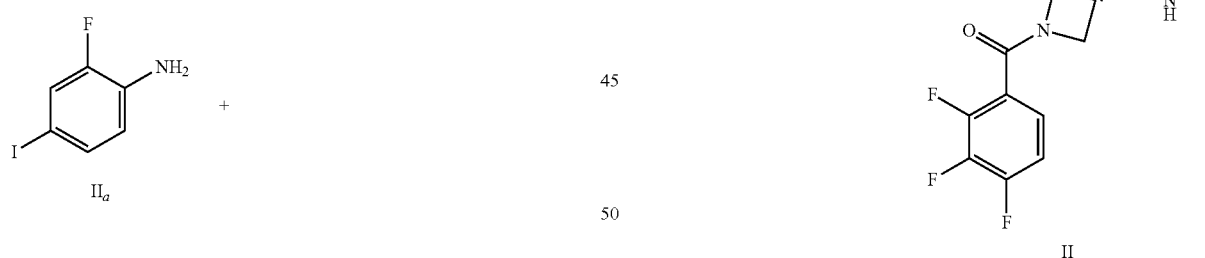

and (b) reacting a compound of formula II with a compound of formula II$_a$ as previously described to provide a compound of formula I.

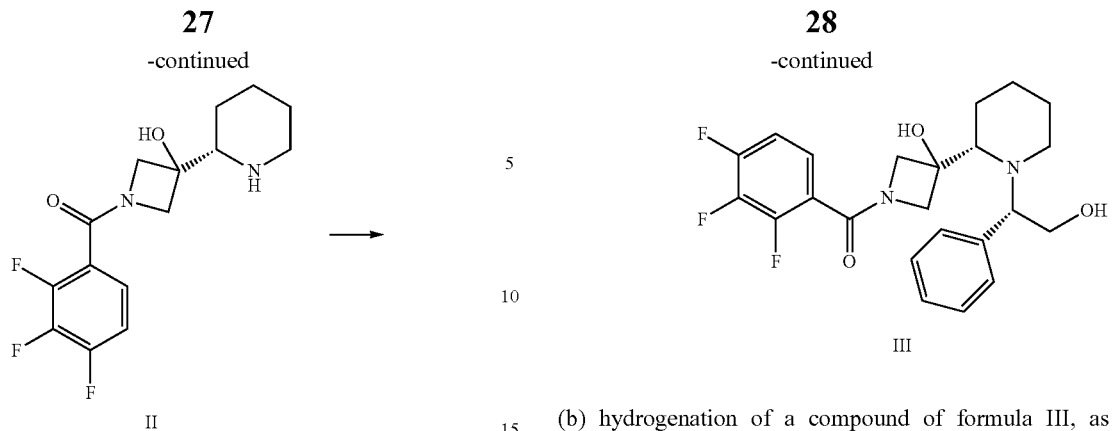

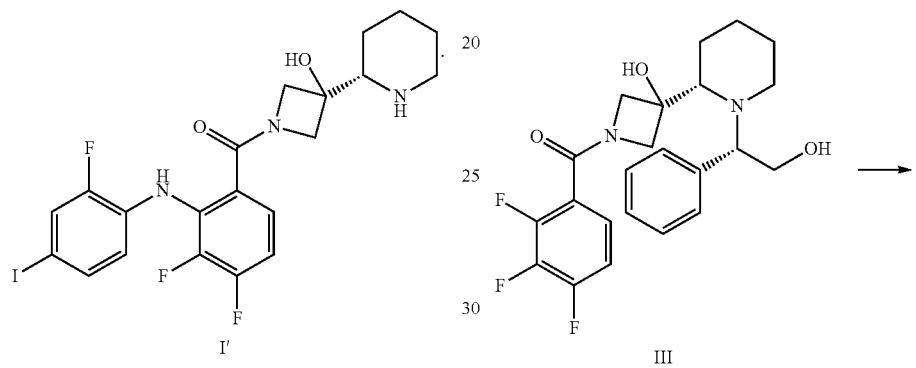

(b) hydrogenation of a compound of formula III, as previously described to provide a compound of formula II;

In particular, steps (a) and (b) can be telescoped.

In another embodiment, the present invention provides a process for the preparation of the compound of formula I', which comprises the following steps:

(a) reacting a compound of formula IV with a compound of formula IV$_a$ as previously described to provide a compound of formula III;

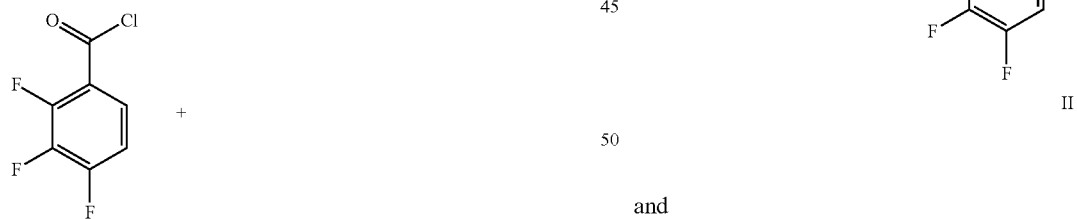

and (c) reacting a compound of formula II with a compound of formula II$_a$ as previously described to provide a compound of formula I'.

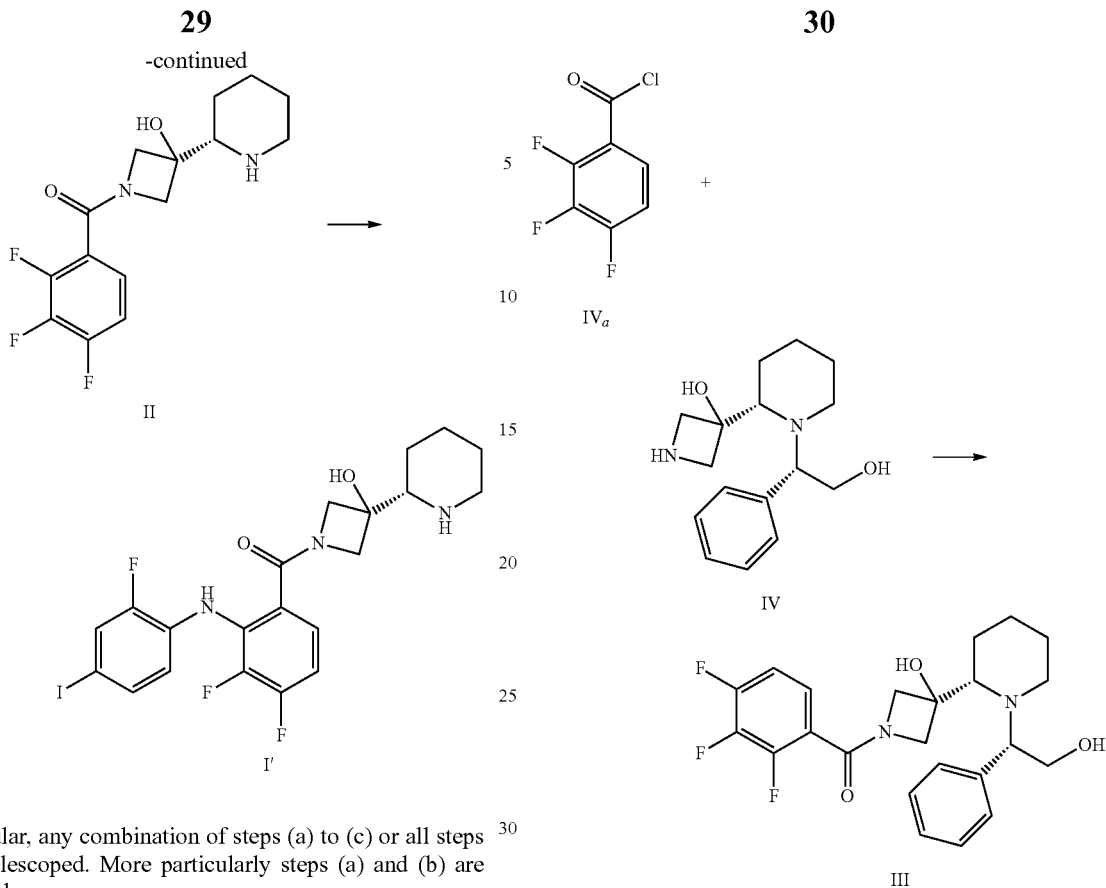

In particular, any combination of steps (a) to (c) or all steps can be telescoped. More particularly steps (a) and (b) are telescoped.

In another embodiment, the present invention provides a process for the preparation of the compound of formula I', which comprises the following steps:

(a) deprotecting the azetidinyl ring of a compound of formula V as previously described to provide a compound of formula IV;

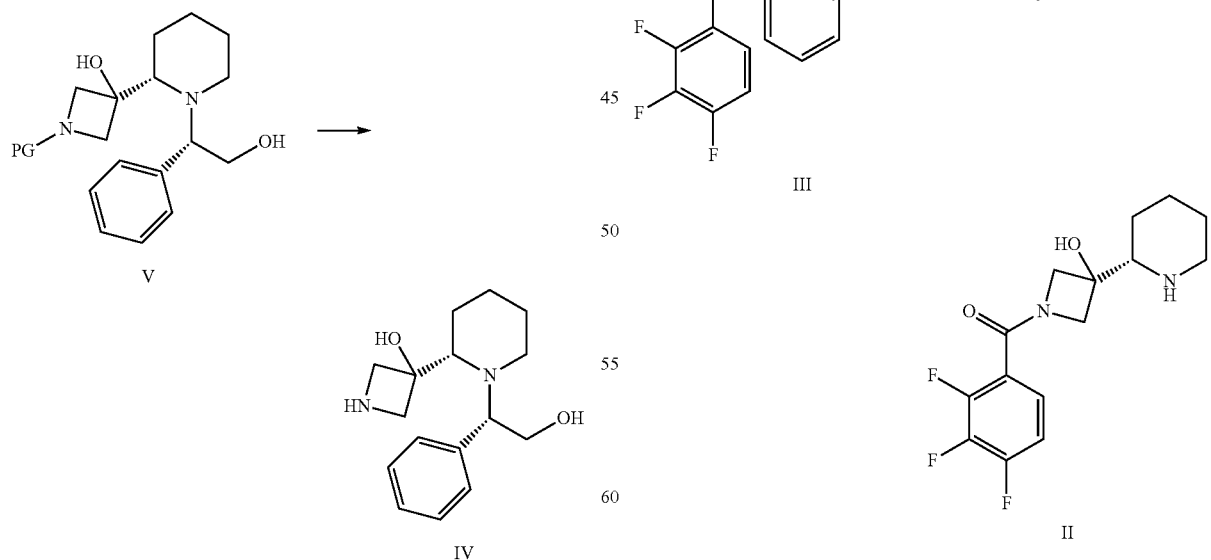

(b) reacting a compound of formula IV with a compound of formula IV$_a$ as previously described to provide a compound of formula III;

(c) hydrogenation of a compound of formula III as previously described to provide a compound of formula II;

and (d) reacting a compound of formula II with a compound of formula II$_a$ as previously described to provide a compound of formula I'.

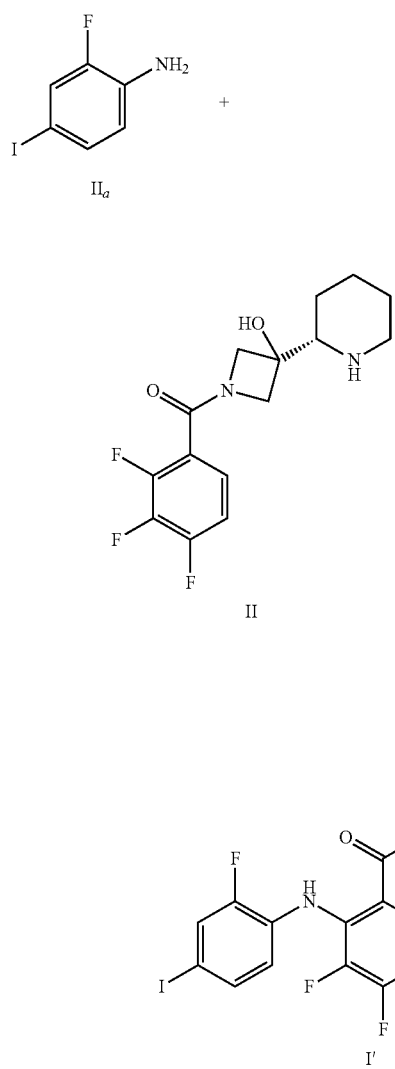

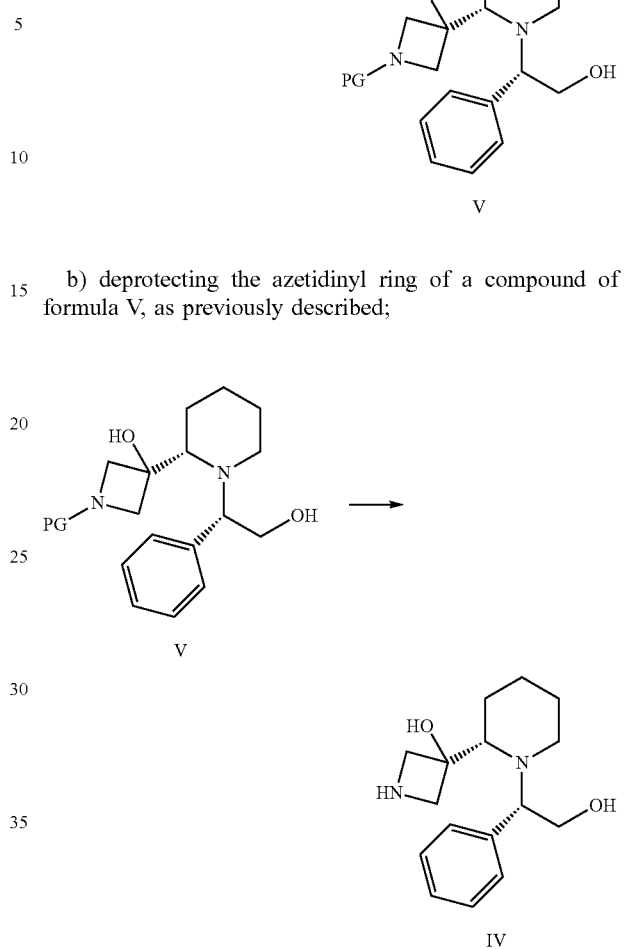

b) deprotecting the azetidinyl ring of a compound of formula V, as previously described;

c) reacting a compound of formula IV with a compound of formula IV$_a$, as previously described;

In particular, any combination of steps a) to d) or all steps can be telescoped. More particularly steps (a) and (c) are telescoped.

In another embodiment, the present invention provides a process for the preparation of the compound of formula I', which comprises the following steps:

a) reacting a compound of formula VI with a reducing agent, as previously described;

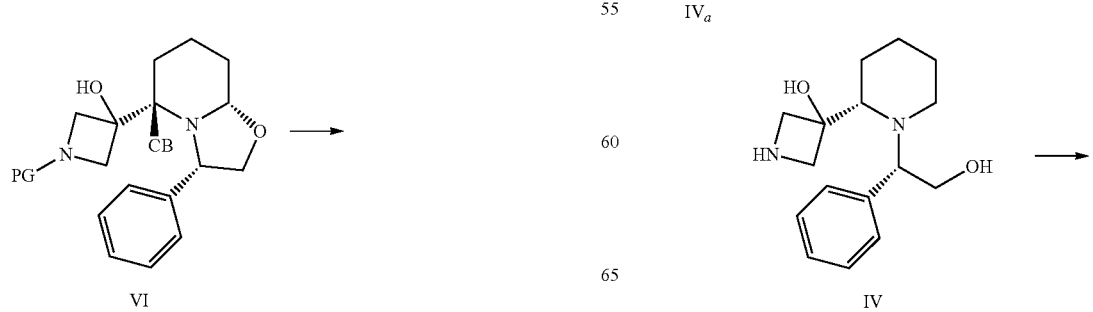

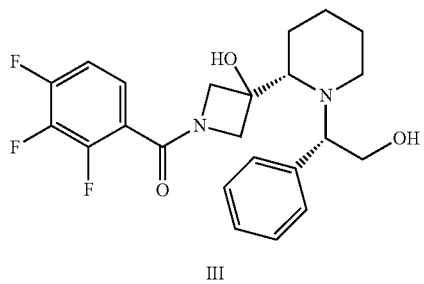

III d) hydrogenation of a compound of formula III, as previously described;

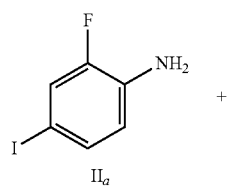

III and e) reacting a compound of formula II with a compound of formula II$_a$, as previously described to provide a compound of formula I'.

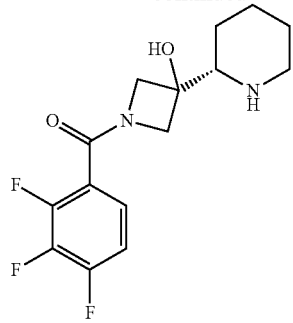

II

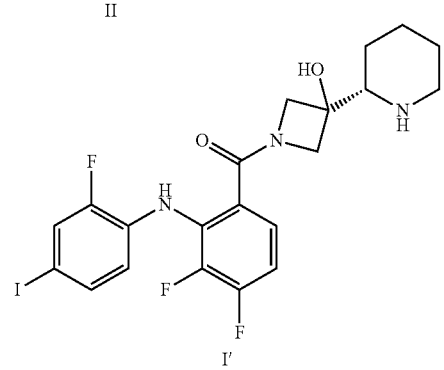

I'

In particular, any combination of steps (a) to (e) or all steps can be telescoped. More particularly steps (a) to (d) are telescoped.

In a further embodiment the present invention provides a process for the preparation of a compound of formula I obtained by any of the processes and conditions mentioned previously.

A further aspect of the present invention provides a compound of formula VI;

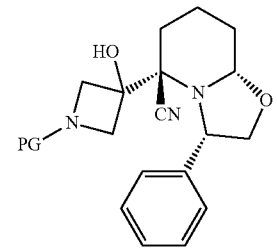

VI wherein PG is an amino protecting group. In one embodiment, PG is tert-butyloxycarbonyl (Boc).

A further aspect of the present invention provides a compound of formula V:

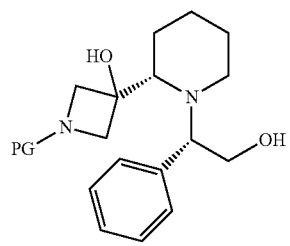

V wherein PG is an amino protecting group. In one embodiment, PG is tert-butyloxycarbonyl (Boc).

A further aspect of the present invention provides a compound of formula IV.

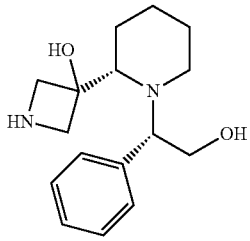

IV

A further aspect of the present invention provides a compound of formula III.

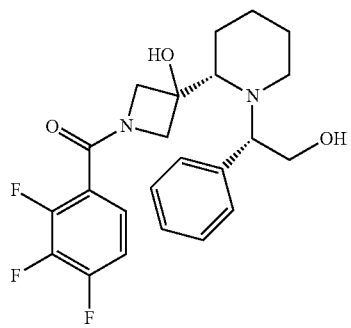

III

A further aspect of the present invention provides a compound of formula II.

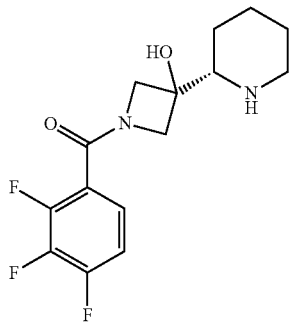

II

Additional Embodiments

The present invention also includes the following additional embodiments.

Embodiment 1. A process for making a compound of formula I:

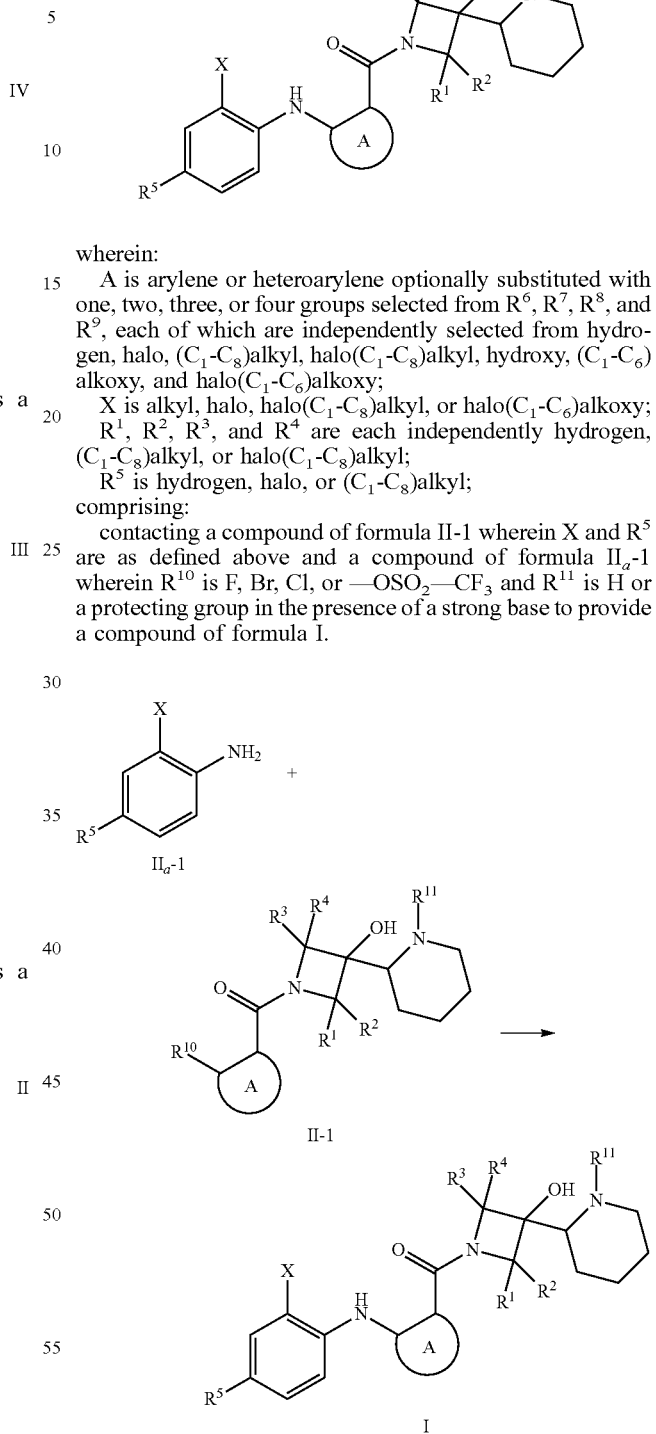

I wherein:
A is arylene or heteroarylene optionally substituted with one, two, three, or four groups selected from $R^6$, $R^7$, $R^8$, and $R^9$, each of which are independently selected from hydrogen, halo, $(C_1-C_8)$alkyl, halo$(C_1-C_8)$alkyl, hydroxy, $(C_1-C_6)$alkoxy, and halo$(C_1-C_6)$alkoxy;
X is alkyl, halo, halo$(C_1-C_8)$alkyl, or halo$(C_1-C_6)$alkoxy;
$R^1$, $R^2$, $R^3$, and $R^4$ are each independently hydrogen, $(C_1-C_8)$alkyl, or halo$(C_1-C_8)$alkyl;
$R^5$ is hydrogen, halo, or $(C_1-C_8)$alkyl;
comprising:
contacting a compound of formula II-1 wherein X and $R^5$ are as defined above and a compound of formula $II_a$-1 wherein $R^{10}$ is F, Br, Cl, or —OSO$_2$—CF$_3$ and $R^{11}$ is H or a protecting group in the presence of a strong base to provide a compound of formula I.

Embodiment 2. The process of any one of embodiments 1 or 2, wherein X and $R^5$ in a compound of formula $II_a$-1 are each independently F, Cl, Br, or I.

Embodiment 3. The process of any one of embodiments 1 to 3, wherein X is F and $R^5$ is I.

Embodiment 4. The process of any one of embodiments 1 to 3 wherein the compound of formula II-1 is the compound of formula II-2,

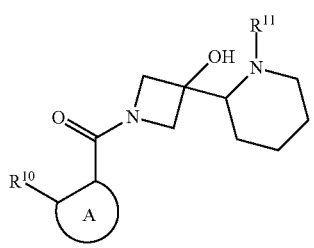

wherein R[11] is H or protecting group and Ring A is optionally substituted with one, two, three or four groups selected from R[6], R[7], R[8], and R[9], each of which are independently selected from halo, $(C_1-C_8)$alkyl, halo$(C_1-C_8)$alkyl, $(C_1-C_6)$alkoxy, and halo$(C_1-C_6)$alkoxy.

Embodiment 5. The process of any one of embodiments 1 to 4, wherein the compound of formula II-1 is the compound of formula II-3,

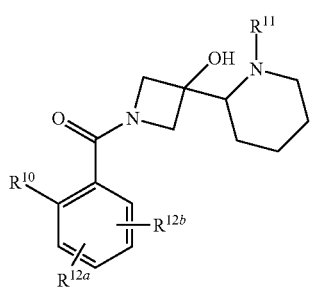

wherein R[11] is as defined previously; R[10] is F, Cl, Br, I, or OSO$_2$CF$_3$; and R[12a] and R[12b] are each independently F, Cl, Br, I, alkyl, haloalkyl, alkoxy, or haloalkoxy.

Embodiment 6. The process of embodiment 5, wherein R[10] in the compound of formula II-3 is F, Cl, Br, or I, and R[12a] and R[12b] are each independently F, Cl, Br, alkyl, haloalkyl, alkoxy, or haloalkoxy.

Embodiment 7. The process of any one of embodiments 1 to 6, wherein R[10] in the compound of formula II-3 is F and R[12a] and R[12b] are each independently F, Cl, alkyl, or alkoxy.

Embodiment 8. The process of any of embodiments 1-7 wherein the strong base is selected from the group consisting of butyllithium, t-butyllithium, the lithium, sodium, or potassium salts of mono or bis-substituted alkyl or aromatic amines, and silylalkyl or silylaromatic amines.

Embodiment 9. The process of any of embodiments 1-8, wherein the strong base is selected from the group consisting of the lithium, sodium, or potassium salts of diisopropyl amine, bis(trimethylsilyl)amine, diethylamine, and dimethylamine.

Embodiment 10. The process of any one of embodiments 1 to 9, wherein the strong base is lithium bis(trimethylsilyl)amide.

Embodiment 11. The process of any one of embodiments 1 to 10, wherein reaction is performed in the presence of a solvent which is tetrahydrofuran.

Embodiment 12. The process of any of embodiments 1 to 11, wherein the compound of formula II$_a$-1 is a compound of formula II$_a$; the compound of formula II-1 is a compound of formula I; and the compound of formula I is a compound of formula I'.

Embodiment 13. A process for preparing a compound of formula II, comprising deprotecting a compound of formula III,

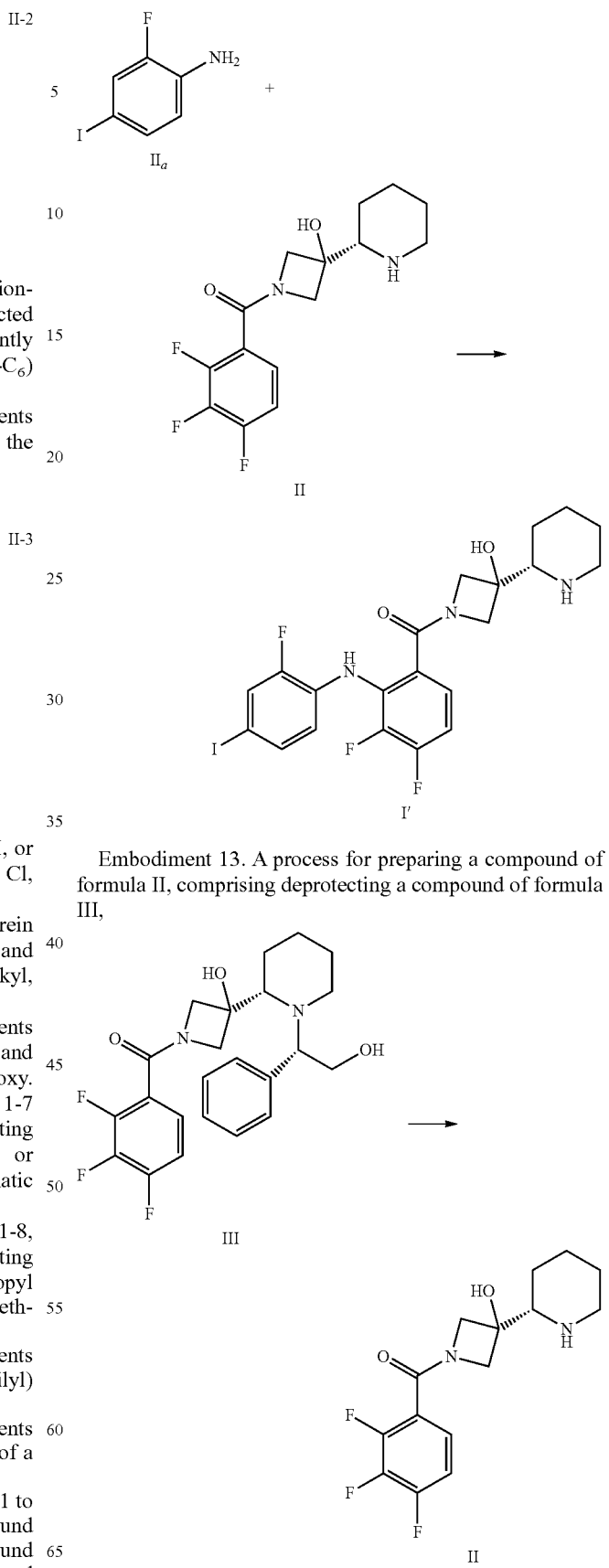

wherein deprotection comprises hydrogenation using H₂ in the presence of a heterogeneous transition metal hydrogenation catalyst or treatment with chloroethyl chloroformate in the presence of MeCN or Na/NH₃.

Embodiment 14. The process of embodiment 13, wherein the heterogeneous transition metal hydrogenation catalyst is selected from the group consisting of a Raney catalyst, Pd/C, Pd(OH)₂/C, Pd(OAc)₂, Au/TiO₂, Rh/C, Ru/Al₂O₃, Ir/CaCO₃, Pt/C, and Palladium(0) microencapsulated in polyurea matrix as a 45 percent mixture of nanoparticles of palladium approximately 2 nm in size in water, containing 0.4 mmol/g Pd(0) (dry basis), where the unit weight includes the weight of water (NP Pd(0) Encat™ 30), or a mixture thereof.

Embodiment 15. The process of embodiment 14, wherein the heterogeneous transition metal hydrogenation catalyst is Pd/C.

Embodiment 16. A process for preparing a compound of formula III, comprising contacting a compound of formula IV$_a$ with a compound of formula IV.

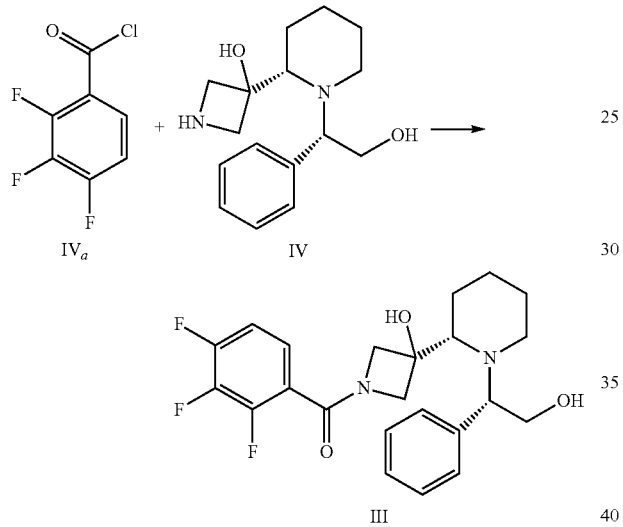

Embodiment 17. The process of embodiment 16 in the presence of an inorganic base which is an alkali or alkali earth metal hydroxide, phosphate, or carbonate.

Embodiment 18. The process of any one of embodiments embodiment 16 to 17, wherein the inorganic base is selected from the group consisting of LiOH, NaOH, KOH, CsOH, NH₄OH, RbOH, Mg(OH)₂, Ca(OH)₂, Ba(OH)₂, Li₂CO₃, Na₂CO₃, K₂CO₃, Cs₂CO₃, (NH₄)₂CO₃, and K₃PO₄.

Embodiment 19. The process of any one of embodiments 16 to 18, wherein the inorganic base is K₃PO₄, K₂CO₃, or KOH.

Embodiment 20. A process for preparing a compound of formula IV, comprising deprotecting a compound of formula V:

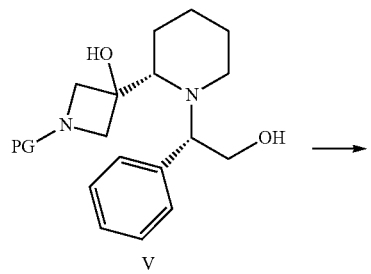

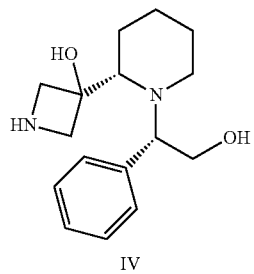

wherein PG is an amino protecting group selected from the group consisting of FMoc, CBz, or BOC protecting group.

Embodiment 21. The process of embodiment 20, wherein the protecting group is a BOC protecting group.

Embodiment 22. A process for preparing a compound of formula V wherein PG is an amino protecting group, comprising reducing a compound of formula VI with a reducing agent selected from the group consisting of borohydrides.

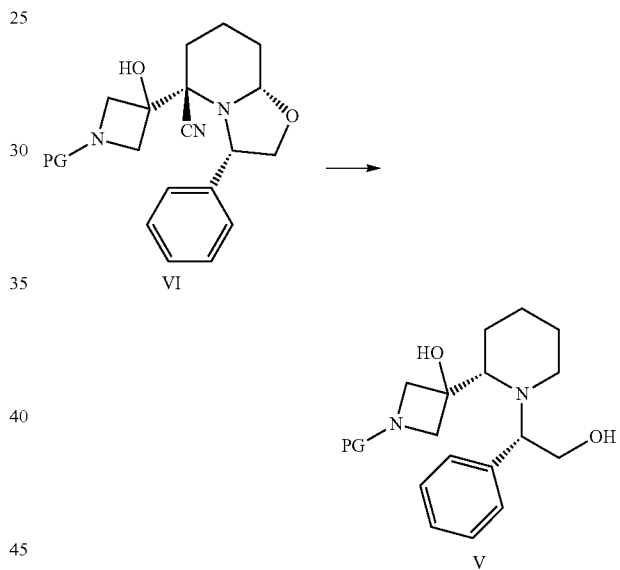

Embodiment 23. A process for preparing a compound of formula VI comprising reacting a compound of formula VII with a compound of formula VII$_a$ in the presence of base wherein PG is an amino protecting group.

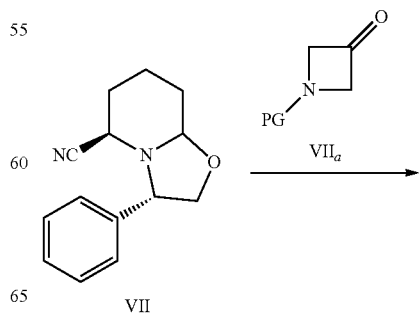

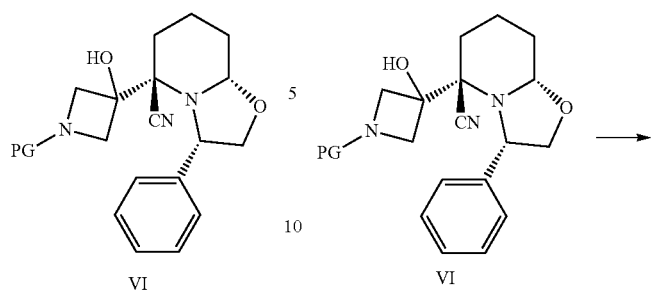

Embodiment 24. A process for the preparation of the compound of formula I'

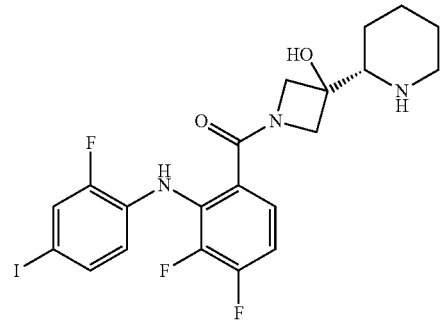

which comprises the following steps:

1) reacting a compound of formula VII with a compound of formula VII$_a$ to provide a compound of formula VI;

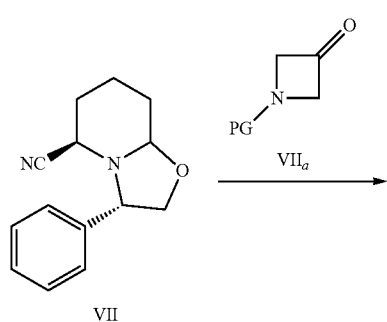

2) reducing a compound of formula VI with a reducing agent selected from the group consisting of borohydrides to provide a compound of formula V;

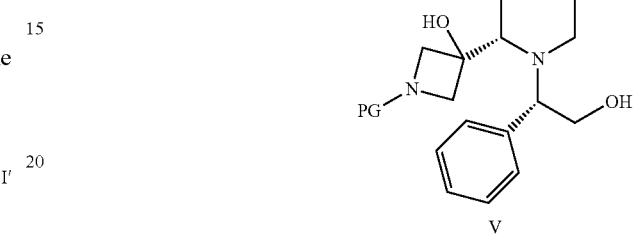

3) deprotecting the azetidinyl ring of a compound of formula V to provide a compound of formula IV;

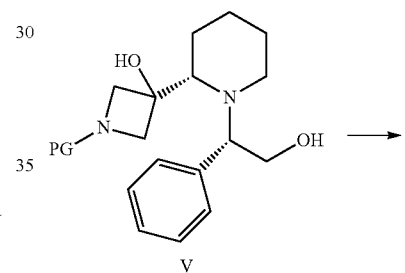

4) reacting a compound of formula IV with a compound of formula IV$_a$ to provide a compound of formula III;

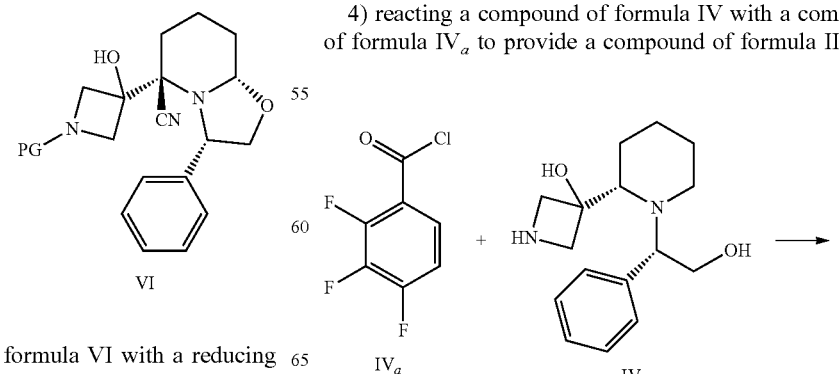

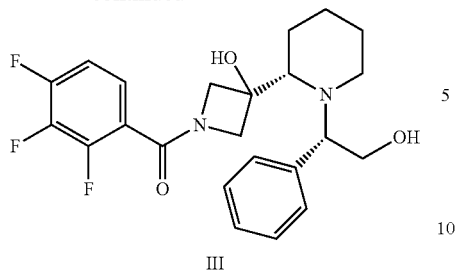

III 5) hydrogenation of a compound of formula III to provide a compound of formula II;

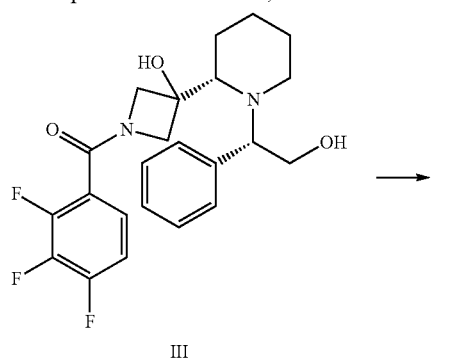

III and 6) reacting a compound of formula II with a compound of formula II$_a$ to provide a compound of formula I'.

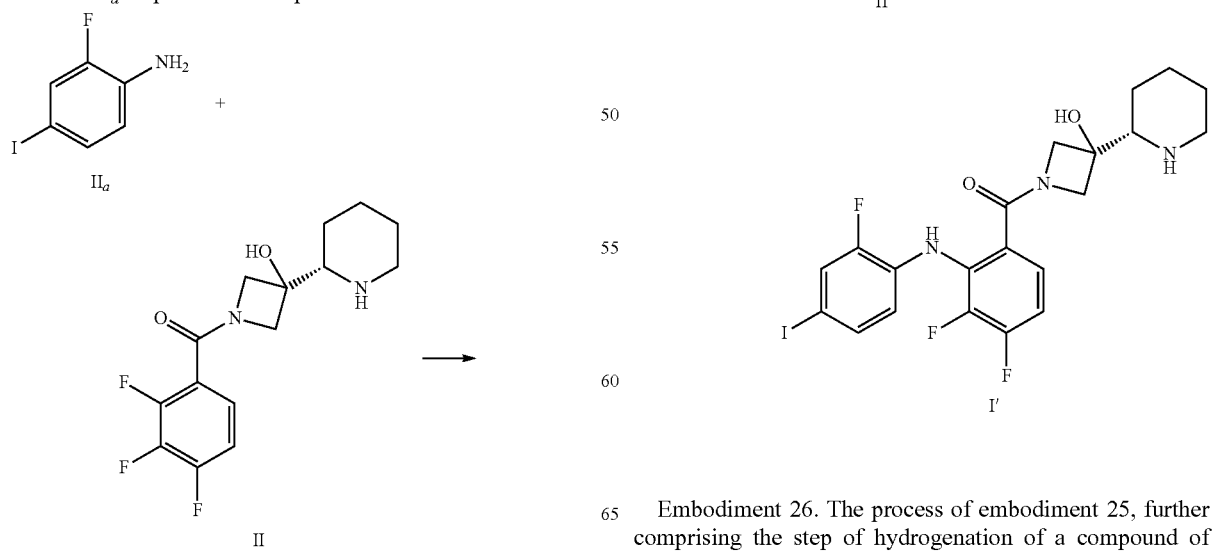

Embodiment 25. A process for the preparation of the compound of formula I' which comprises contacting a compound of formula II and compound of formula II$_a$ in the presence of a strong base to provide a compound of formula I'.

Embodiment 26. The process of embodiment 25, further comprising the step of hydrogenation of a compound of formula III to provide a compound of formula II.

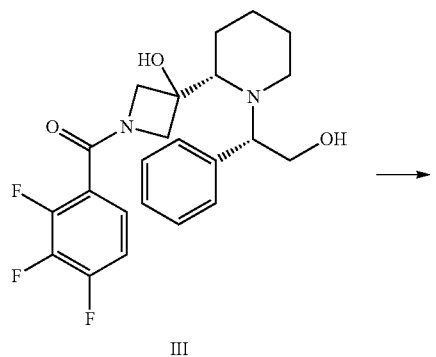

III

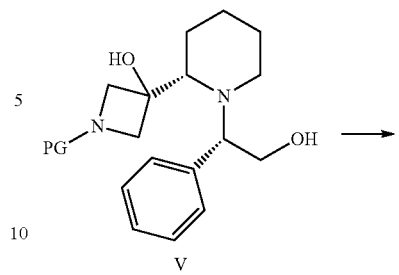

V

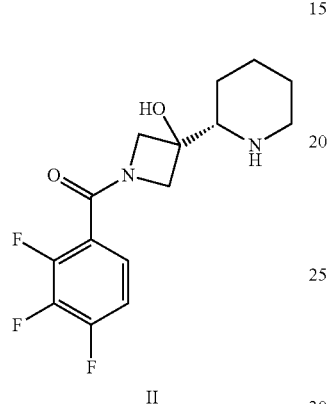

II

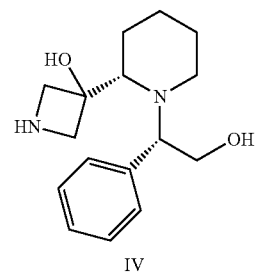

IV

Embodiment 27. The process of embodiment 26, further comprising the step of reacting a compound of formula IV with a compound of formula IV$_a$ to provide a compound of formula III.

Embodiment 29. The process of embodiment 28, further comprising reducing a compound of formula VI with a reducing agent selected from the group consisting of borohydrides to provide a compound of formula V.

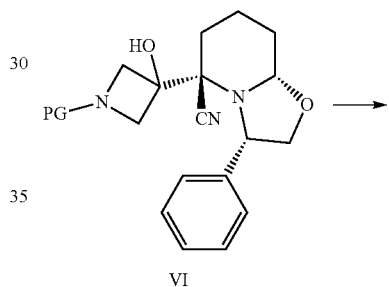

VI

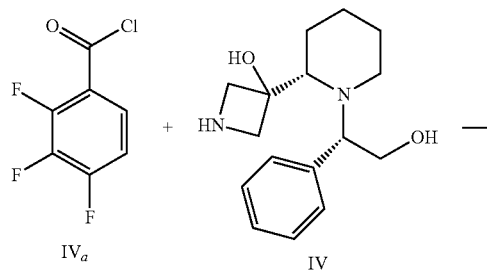

IV$_a$     IV

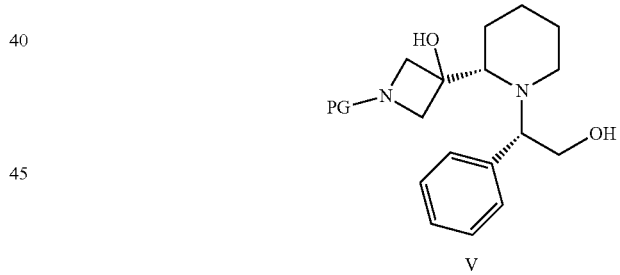

V

Embodiment 30. The process of embodiment 29, further comprising reacting a compound of formula VII with a compound of formula VII$_a$ in the presence of base.

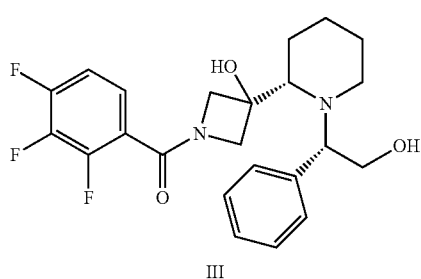

III

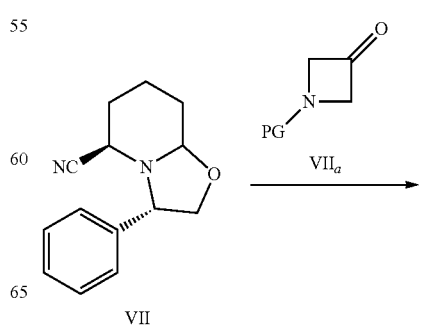

VII     VII$_a$

Embodiment 28. The process of embodiment 27, further comprising the step of deprotecting the azetidinyl ring of a compound of formula V.

Embodiment 32. The compound of embodiment 31, wherein PG in the compound of formulas VI and V is BOC.

Synthesis

Compounds of this invention can be made by the synthetic procedures described below. The starting materials and reagents used in preparing these compounds are either available from commercial suppliers such as Sigma Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure and over a temperature range from about −78° C. to about 150° C., more preferably from about 0° C. to about 125° C., and most preferably at about room (or ambient) temperature, e.g., about 20° C. Unless otherwise stated (as in the case of a hydrogenation), all reactions are performed under an atmosphere of nitrogen.

The compounds disclosed and claimed herein have asymmetric carbon atoms or quaternized nitrogen atoms in their structure and may be prepared through the through syntheses described herein as single stereoisomers, racemates, and as mixtures of enantiomers and diastereomers. The compounds may also exist as geometric isomers. All such single stereoisomers, racemates, and mixtures thereof, and geometric isomers are intended to be within the scope of this invention.

Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereomeric salts or complexes which may be separated, for example, by crystallization; via formation of diastereomeric derivatives which may be separated, for example, by crystallization; selective reaction of one enantiomer with an enantiomer-specific reagent, for example enzymatic oxidation or reduction, followed by separation of the modified and unmodified Embodiment 31. A compound which is:

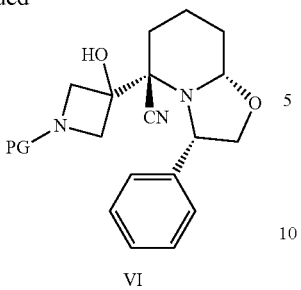

(VI)

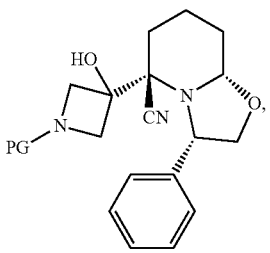

wherein PG is a protecting group;

(V)

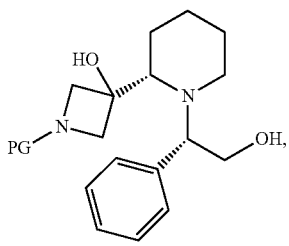

wherein PG is an amino protecting group;

(IV)

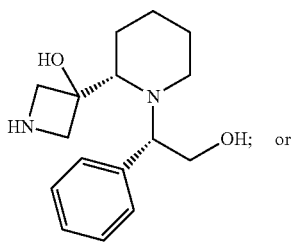
or (III)

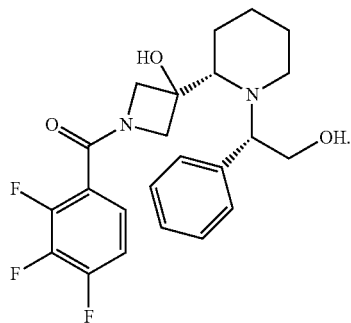

enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomers may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The methods of the present invention may be carried out as semi-continuous or continuous processes, more preferably as continuous processes.

The present invention as described above unless indicated otherwise may be carried out in the presence of a solvent or a mixture of two or more solvents. In particular the solvent is an aqueous or an organic solvent such as the ether-like solvent (e.g. tetrahydrofuran, methyltetrahydrofuran, diisopropyl ether, t-butylmethyl ether or dibutyl ether)aliphatic hydrocarbon solvent (e.g. hexane, heptane or pentane), saturated alicyclic hydrocarbon solvent (e.g. cyclohexane or cyclopentane) or aromatic solvent (e.g. toluene, o- m- or p-xylene or t-butyl-benzene) or mixture thereof.

The starting materials and reagents, which do not have their synthetic route explicitly disclosed herein, are generally available from commercial sources or are readily prepared using methods well known to the person skilled in the art.

In general, the nomenclature used in this Application is based on AUTONOM™ 2000, a Beilstein Institute computerized system for the generation of IUPAC systematic nomenclature. Chemical structures shown herein were prepared using MDL ISIS™ version 2.5 SP5. Any open valency appearing on a carbon, oxygen or nitrogen atom in the structures herein indicates the presence of a hydrogen atom.

Compounds of formula I, particularly the compound of formula I', can be prepared as generally depicted in Scheme 1. Reaction of commercially available (3S,5R,8aS)-3-phenyl-hexahydro-oxazolo[3,2-a]pyridine-carbonitrile VII$_a$ with commercially available tert-butyl-3-oxo-1-azetidinecarboxylate VII in the presence of base provides compound VI. Compound VI is treated with a hydride reducing agent such as sodium cyanoborohydride in the presence of acid, followed by treatment with aqueous sodium hydroxide, to provide compound V. Deprotection of V using acid gives compound IV, which is coupled to acid chloride IV$_a$ in the presence of a catalytic amount of pyridine to provide III. Hydrogenation of III provided piperidine derivative II. Finally, coupling of II with 2-fluoro-4-iodo aniline II$_a$ provides the desired compound.

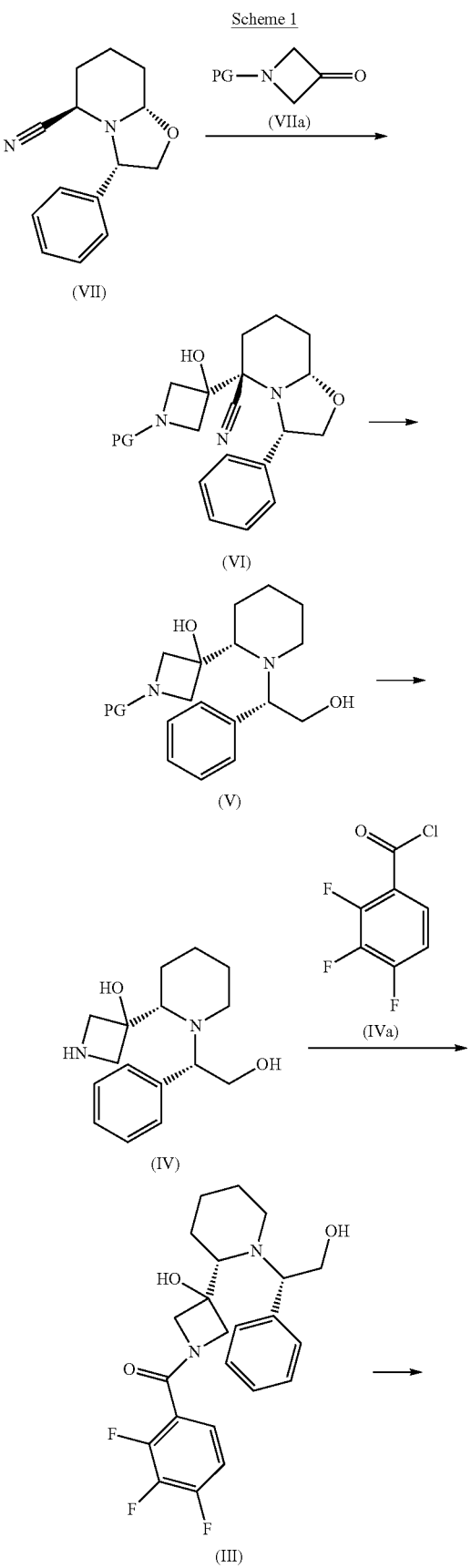

-continued

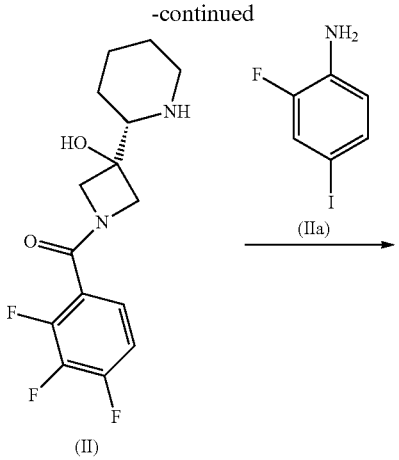

The following examples are provided for the purpose of further illustration and are not intended to limit the scope of the claimed invention.

EXAMPLE 1

Synthesis of 3-((3S,5R,8aS)-5-Cyano-3-phenyl-hexahydro-oxazolo[3,2-a]pyridin-5-yl)-3-hydroxy-azetidine-1-carboxylic acid tert-butyl ester

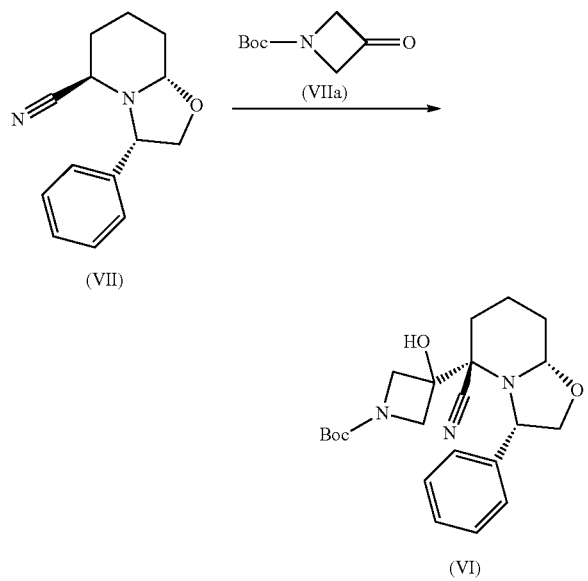

A mixture of (3S,5R,8aS)-3-phenyl-hexahydro-oxazolo[3,2-a]pyridine-carbonitrile (20.0 g, 87.6 mmol, 1.0 eq.) and dimethyltetrahydropyrimidone (DMPU, 11.3 g, 87.6 mmol, 1.0 eq.) in THF (95.1 mL) was stirred for 10 min until a clear solution was observed. The mixture was then cooled to −70 to −80° C. and lithium diisopropylamide (28% soln. in heptane, THF and ethylbenzene) (35.2 g, 92 mmol, 1.05 eq.) was added over 30 min while maintaining the internal temperature between −70 to −80° C. After complete addition, the mixture was stirred at −70 to −80° C. for an additional 2 h, followed by dosing a solution of 3-oxo-azetidine-1-carboxylic acid tert-butyl ester (16.2 g, 94.6 mmol, 1.08 eq.) in THF (16.4 g) over 30 min while maintaining the internal temperature between −70 to −80° C. After complete dosage, the reaction mixture was stirred at −70 to −80° C. for 1 h.

In a separate flask, a solution of sodium chloride (10.3 g), deionized water (103.0 g) and acetic acid (5.29 g, 87.6 mmol, 1.0 eq.) was prepared and cooled to 0° C. The reaction mixture was dosed onto the quench mixture over 30 min while maintaining the internal temperature at less than 10° C. The flask of the reaction mixture was rinsed with THF (26.7 g) and the rinse was combined with the quenched mixture. After vigorously stirring for 20 min at 5° C., agitation was stopped and the layers were allowed to separate. The lower aqueous phase was discarded. Ethyl acetate (61.8 g) and deionized water (68.5 g) were added to the organic phase. After vigorously stirring at 5° C. for 10 min, agitation was stopped, the layers were allowed to separate, and the lower aqueous phase was discarded. The washing procedure was repeated once with deionized water (68.5 g).

The organic phase was concentrated under reduced pressure (jacket temperature approximately 40-45° C., pressure=200-180 mbar) until a total volume of approximately 120 mL of distillate was collected resulting in a yellowish solution. The vacuum was released and heptane (102.0 g) was added over 10 min. Distillation under reduced pressure was continued (jacket temperature approximately 35-40° C., pressure approximately 250-110 mbar) by adding heptane (177 g) at a rate so that the residual volume was kept constant. After 10 min of distilling, a thick, stirrable suspension was obtained. The vacuum was released and isopropanol (10.2 g) was added over 15 min at 35° C. The suspension was heated at 45° C. and stirred for 30 min. Thereafter, the suspension was cooled to 0° C. over 2 h and held at 0° C. for 1 h. The suspension was filtered over a glass filter. The flask and filter cake were rinsed with pre-cooled (approximately 5° C.) heptane (46.6 g), and the wet cake was dried overnight at 40° C. under reduced pressure until constant weight to yield the title compound as slightly beige crystals. HPLC purity: 91.9%-area. Mp. (DSC): extrapolated peak: 151.80° C. $^1$H-NMR (600 MHz, CDCl$_3$): δ 7.30-7.50 (m, 5 H), 4.17-4.27 (m, 3 H), 3.94-4.01 (m, 2 H), 4.11-4.1 (m, 2 H), 4.09 (d, 1 H), 3.95 (d, 1 H), 3.87 (dd, 1 H), 3.76 (dd, 1 H), 3.54-3.70 (br, 1 H), 2.85-3.03 (br, 1 H), 2.18-2.25 (m, 1 H), 2.12 (br, 1 H), 1.97-2.04 (m, 1 H), 1.85-1.94 (m, 1 H), 1.61-1.79 (m, 3 H), 1.41 (s, 9 H). MS (EI): m/z=400.48 ([M+H]$^+$, 100%).

EXAMPLE 2

Synthesis of 3-Hydroxy-3-[(S)-1-((S)-2-hydroxy-1-pehyl-ethyl)-piperidin-2-yl]azetidine-1-carboxylic acid tert-butyl ester

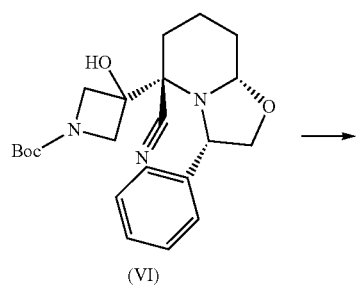

(VI)

A mixture of 3-((3S, 5R, 8aS)-5-cyano-3-phenyl-hexahydro-oxazolo[3,2-a]pyridin-5-yl)-3-hydroxy-azetidine-1-carboxylic acid tert-butyl ester (12.0 g, 30.0 mmol, 1.0 eq.) and sodium cyanoborohydride (3.18 g, 50.6 mmol, 1.68 eq.) in EtOH (70 mL) was heated to 30° C. and slowly added within two h to a warm mixture (70° C.) of acetic acid (3.63 ml, 63.5 mmol, 2.1 eq.) in EtOH (20 mL). The resulting mixture was subsequently stirred for another 3 h at 70 to 75° C. After complete reaction, the mixture was cooled to 23° C. and slowly dosed within 30 min into a mixture of toluene (100 mL) and aqueous NaOH (60 g, 10%-w/w) and stirred for 15 min. The reaction flask was rinsed with the quenched mixture. The layers were separated, and the organic phase was washed with toluene (30 mL). The combined organic phases were concentrated under vacuum (200 to 85 mbar at 35 to 40° C. jacket temperature) until 80 mL (70.82 g) of a yellowish product solution was obtained. HPLC purity: 97.6% area.

For analytical purposes, the product solution was fully concentrated in the rotary evaporator, treated with EtOH and again fully concentrated resulting in 19.2 g of a foamy product. The residue was dissolved in a mixture of ethyl acetate (30 mL) and MeOH (15 mL) and purified by flash chromatography over 120 g silica gel using ethyl acetate as eluent. Fractions 3 to 5 of 6 fractions of 100 mL each were combined and fully concentrated under vacuum in the rotary evaporator resulting in 14.6 g of colorless foam. This residue was again dissolved in a minimum of a mixture of heptane/ethyl acetate 2:1 (v/v) and purified by flash chromatography over 190 g of silica gel using heptane/ethyl acetate 2:1 (v/v) as eluent. After a forerun of 700 mL, ten subsequent fractions (800 mL total) were combined, fully evaporated in the rotary evaporator under vacuum (bath temperature 35° C., pressure≥20 mbar) and the residue was dried overnight at 35° C. and under vacuum until constant weight to yield the title compound as a colorless solid. Mp. (DSC): extrapolated peak: 220.9° C. (melting accompanied by exothermic decomposition). $^1$H-NMR (600 MHz, CDCl$_3$): δ 7.38-7.41 (m, 2 H), 7.34-7.38 (m, 2 H), 7.27-7.30 (m, 1 H), 4.28-4.50 (br, 1 H), 4.19 (dd, 1 H), 4.11-4.1 (m, 2 H), 4.09 (d, 1 H), 3.95 (d, 1 H), 3.87 (dd, 1 H), 3.83 (t, 1 H), 3.08-3.16 (m, 1 H), 2.85 (ddd, 1 H), 2.57 (ddd, 1 H), 1.76-1.84 (m, 1 H), 1.68-1.75 (m, 1 H), 1.53-1.58 (m, 1 H), 1.41-1.48 (bs, 9 H), 1.31-1.41 (m, 2 H), 1.21-1.31 (m, 2 H). MS (EI): m/z=377.24 ([M+H]$^+$, 100%). EA for C$_{21}$H$_{32}$N$_2$O$_4$: calcd: C 66.99, H 8.57, N 7.44; found C 67.38, H 8.50, N 7.29.

EXAMPLE 3

Synthesis of 3-[(S)-1-((S)-2-Hydroxy-1-phenyl-ethyl)-piperidin-2-yl]-azetidin-3-ol di hydrochloride

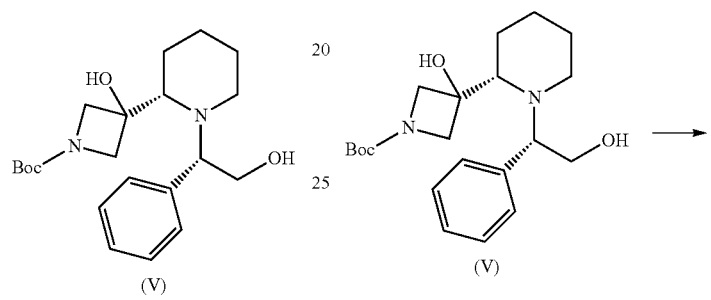

A solution of 3-hydroxy-3-[(S)-1-((S)-2-hydroxy-1-phenyl-ethyl)-piperidin-2-yl]azetidine-1-carboxylic acid tent-butyl ester (69.8 g, 29.6 mmol, 1.0 eq.) in toluene was treated at 23-27° C. within 12 min with a mixture of water (30.1 g) and HCl (37%, 7.22 g, 73.3 mmol, 2.5 eq.) and stirred for 10 min. The resulting biphasic mixture was heated to 50° C. within 30 min and kept stirring for 4 h at 50° C. After complete conversion, the mixture was cooled down to room temperature and the phases were allowed to separate. The aqueous phase was washed with toluene (36 mL) and the phases were allowed to separate, resulting in 44.2 g of a yellowish aqueous product solution. HPLC purity: 96.3%-area.

For analytical purposes, the product solution was fully concentrated in the rotary evaporator (bath temperature 45° C.). The yellow oily residue was dissolved in MeOH (190 mL) and again fully concentrated in the rotary evaporator and under vacuum. The residue was taken up in a minimum of a mixture of MeOH/ethyl acetate 1:1 (v/v) and purified by flash chromatography over silica gel (150 g) using a mixture of MeOH/ethyl acetate 1:1 (v/v) as eluent. A forerun of 400 mL was taken and discarded and the subsequent fractions (1.5 L) were combined and completely concentrated in the rotary evaporator under vacuum (bath temperature 40° C., pressure ≥20 mbar) resulting in a yellow oil that was dissolved in MeOH (20 mL). The oil was added drop-wise at room temperature to ethyl acetate (80 mL), whereupon the product precipitated. The solids were filtered and rinsed with ethyl acetate (30 mL). Drying overnight at 30° C. under vacuum until constant weight resulted in the title compound (22.0 g) as a colorless solid. Mp. (DSC): $T_{onset}$ 114.2° C., extrapolated peak: 123.4° C. $^1$H NMR (600 MHz, DMSO-$d_6$): δ 9.50-9.64 (br, 1 H), 8.91-9.03 (br, 1 H), 7.78 (s, 1 H), 7.62-7.56 (m, 2 H), 7.41-7.52 (m, 3 H), 6.03 (bs, 1 H), 4.56-4.67 (m, 1 H), 4.45 (dd, 1 H), 4.25-4.33 (m, 2 H), 4.23 (dd, 1 H), 4.18 (dd, 1 H), 3.95-4.05 (m, 1 H), 3.83 (dd, 1 H), 3.45-3.54 (m, 1 H), 3.26-3.40 (m, 1 H), 1.67-1.86 (m, 4 H), 1.55-1.65 (m, 1 H), 1.37-1.51 (m, 1 H). MS (EI): m/z=277 ([M+H]$^+$ of free base 100%). EA for $C_{16}H_{26}N_2O_2Cl_2$, corrected for water (9.2%-w/w) and HCl (2.1 eq. instead of 2.0 eq.): calcd: C 49.44, H 7.80, N 7.21, O 16.40, Cl 19.15; found C 48.76, H 7.48, N 7.36, O 16.44, Cl 19.11.

EXAMPLE 4

{3-Hydroxy-3-[(S)-1-((S)-2-hydroxy-1-phenyl-ethyl)-piperidin-2-yl]-azetidin-1-yl}-(2,3,4-trifluoro-phenyl)-methanone

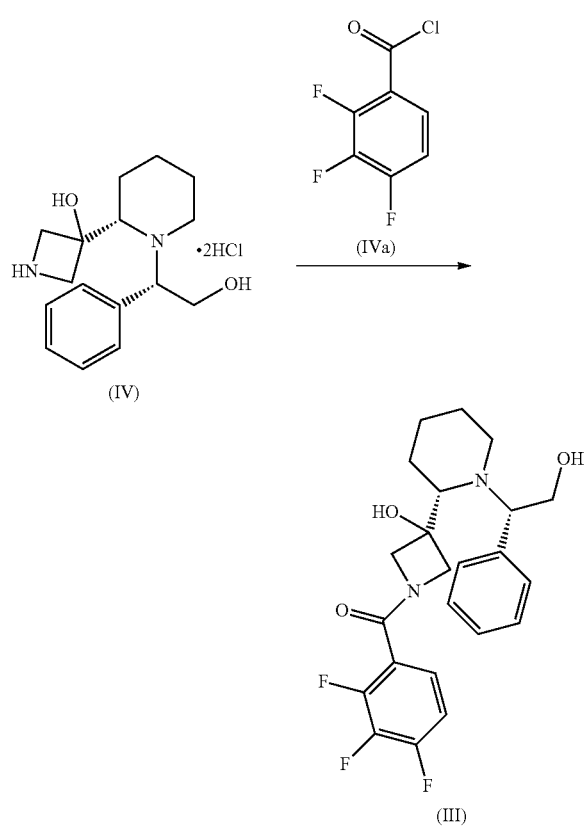

2,3,4-Trifluoro-benzoyl chloride 2,3,4-Trifluorobenzoic acid (100 g, 568 mmol, 1.0 eq.) was suspended in toluene (1000 mL) and treated with pyridine (0.254 mL, 3.15 mmol, 0.0055 eq.). The resulting suspension was heated to 60 to 70° C., whereupon the mixture became a clear yellowish solution. At this temperature, oxalyl chloride (94.4 g, 729 mmol, 1.3 eq.) was slowly added over 156 minutes. After complete addition, the mixture was kept stirring for 10 min until complete. Toluene (360 mL) was partially removed by distillation under vacuum (jacket temperature: 60 to 70° C., pressure: 200 to 100 mbar). The solution was cooled to room temperature, resulting in 636 g of a yellowish and slightly turbid solution that was stored under $N_2$ atmosphere and used in the subsequent step without any further treatment. HPLC purity: 99.2%-area.

{3-Hydroxy-3-[(S)-1-((S)-2-hydroxy-1-phenyl-ethyl)-piperidin-2-yl]-azetidin-1-yl}-(2,3,4-trifluoro-phenyl)-methanone The aqueous solution of 3-[(S)-1-((S)-2-hydroxy-1-phenyl-ethyl)-piperidin-2-yl]-azetidin-3-ol di hydrochloride (43.5 g) was treated with EtOH (24 mL) and stirred for 10 min at room temperature. To this mixture was added a solution of tripotassium phosphate (28.8 g, 136 mmol, 4.7 eq.) in 261 mL water within 14 min at a batch temperature of 10 to 20° C. and the mixture was stirred for 15 min at 15° C. (pH 11.9). To this solution was added via dropping funnel 34 g of the above described 2,3,4-Trifluoro-benzoyl chloride solution (34.0 g, 29.8 mmol, 1.0 eq.) over 32 min at a batch temperature of 10 to 20° C. while vigorously stirring. The dropping funnel was rinsed with toluene (1.2 ml) and the biphasic mixture was stirred at room temperature for 60 min. The layers were allowed to separate, and the aqueous phase was discarded. The organic phase was washed with a solution of sodium carbonate (3.36 g, 31.5 mmol, 1.09 eq.) in water (42 g) and stirred for 30 min at room temperature. The layers were allowed to separate, and the organic phase was washed with aqueous sodium chloride (30 g, 10%-w/w). In the rotary evaporator (bath temperature 50° C., pressure<200 mbar), the organic phase was concentrated to a volume of approximately 30%. The residue was taken up in EtOH (23 mL) and stirred for 5 min at 40 to 50° C. The solution was again concentrated in the rotary evaporator (bath temperature 50° C., pressure less than 200 mbar, 17 ml distillate), resulting in a very viscous oil. The residue was again taken up in EtOH (23 mL) and stirred for 10 min and again further diluted with EtOH (12 mL) in order to reach the target volume (53 mL, 46.06 g). HPLC purity: 85.0%-area.

For analytical purposes, the product solution (90 mL) was filtered and the filter residue was washed with EtOH (15 ml). In the rotary evaporator (bath temperature 40° C., pressure<150 mbar), the solution was completely concentrated, and the residue was taken up in MTBE (40 mL), subsequently again fully concentrated, then taken up in a mixture of ethyl acetate (29 mL) and heptane (40 mL), then fully concentrated, then again taken up in a mixture of MTBE (20 mL) and heptane (50 mL) and again fully concentrated resulting, finally, in a foamy solid (32.5 g). The solid residue (32.0 g) was dissolved in ethyl acetate (20 mL) and purified by flash chromatography over silica gel (150 g) using ethyl acetate as eluent. After a forerun of 200 mL, 6 fractions (800 mL) were combined and completely concentrated in the rotary evaporator (bath temperature: 40° C., pressure ≥20mbar) resulting in 28.0 g of a slightly yellowish oil. At room temperature, the oily residue was taken up in dichloromethane (20 mL), diluted with heptane (150 mL) and again fully concentrated in the rotary evaporator, followed by dissolving the residue in MTBE (20 mL) and again by complete removal of the solvent in the rotary evaporator resulting in a rubber-like foam. This foam was dissolved in toluene (30 mL, room temperature) and dosed over 20 min added drop-wise by dropping funnel at room temperature to heptane (400 mL), whereupon the product started to precipitate. The dropping funnel was rinsed with toluene (4 mL) and the suspension was kept stirring for 1 h at room temperature. The solids were filtered off and the reactor and filter cake were twice rinsed with the filtrate and subsequently with heptane (15 mL). Drying under vacuum at 35° C. until weight constancy resulted in 17.88 g of a colorless solid. HPLC purity: 97.0%-area, residual solvents: toluene (1.2%-w/w) and heptane (2.3%-w/w). Mp (visually): $T_{onset}$: 55-73° C. (melting accompanied by exothermic decomposition). $^1$H NMR (400 MHz, DMSO-$d_6$, 120° C.): δ 7.41-7.47 (m, 2 H), 7.27-7.32 (m, 2 H), 7.21-7.26 (m, 2 H), 7.12-7.19 (m, 1 H), 5.21 (bs, 1 H), 4.35 (bd, 1 H), 4.22 (bs, 1 H), 4.05 (dd, 1 H), 3.91-4.01 (m, 1 H), 3.74-3.90 (m, 4 H), 3.01 (dd, 1 H), 2.75-2.84 (m, 1 H), 2.49-2.59 (m, 1 H), 1.68-1.81 (m, 1 H), 1.51-1.65 (m, 1 H), 1.23-1.50 (m, 3 H), 1.09-1.22 (m, 1 H). MS (EI): m/z=435 ([M+H]$^+$, 100%). EA for $C_{23}H_{25}F_3N_2O_3$, corrected for residual toluene (1.2%-w/w) and heptane (2.3%-w/w): calcd: C 64.38, H 6.07, F 12.66, N 6.22; found C 64.01, H 6.04, F 12.63, N 6.35.

EXAMPLE 5

Synthesis of ((S)-3-Hydroxy-3-piperidin-2-yl-azetidin-1-yl)-(2,3,4-trifluoro-phenyl)-methanone hydrochloride

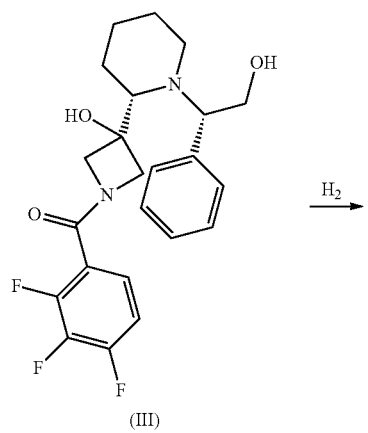

A 185 mL glass autoclave under argon was charged with Pd/C (3.37 g, 1.3 mmol, 0.04 eq, 60.2% ww water, 10% ww Pd on C), water (0.22 g) and a solution of {3-hydroxy-3-[(S)-1-((S)-2-hydroxy-1-phenyl-ethyl)-piperidin-2-yl]-azetidin-1-yl}-(2,3,4-trifluoro-phenyl)-methanone in EtOH (53 mL, 46 g, 29 mmol, 1.0 eq.). The mixture was treated with EtOH (13 mL), Acetic acid (4.15 mL, 72 mmol, 2.5 eq.) and with aqueous hydrochloric acid (2.5 ml, 37%-w/w, 30 mmol, 1.0 eq.). The autoclave was rendered inert, pressurized with 2 bar of $H_2$, and the reaction was run at 2 bar $H_2$ pressure at 25° C. for 12 h. The pressure was released from the autoclave, and the suspension was treated with MeOH (25 mL) and kept stirring for 30 min and filtered under argon protection over filter paper. The autoclave and the filter residue were rinsed with MeOH (4 mL). The combined filtrates were evaporated under reduced pressure to approximately 20-30 percent of the initial volume. The residue was treated with isopropanol (38.5 mL) at 30 to 35° C., stirred for 1 h, cooled to 20 to 25° C., and treated with water (0.58 g) and with aqueous hydrochloric acid (2.5 mL, 37%-ww, 30 mmol, 1.0 eq.). The resulting suspension was concentrated under vacuum at 25 to 35° C. until a volume of approximately 22 mL was reached, and MTBE (31 mL) was added at 25 to 35° C. The final suspension was cooled to 5 to 10° C., stirred for 1 h, and then filtered. The filter cake was rinsed with cold MTBE (12 mL) and dried under vacuum at 35° C. until weight constancy to yield the title compound (5.08 g) as a colorless solid. HPLC purity: 99.6%-area. Mp. (DSC): $T_{onset}$: 246.3° C., extrapolated peak: 248.8° C. (melting accompanied by exothermic decomposition). $^1$H NMR (400 MHz, DMSO-$d_6$, 120° C.): δ 8.59 (bs, 2 H), 7.14-7.48 (m, 2 H), 6.54 (bs, 1 H), 4.39 (dd, 1 H), 4.23 (dd, 1 H), 3.85-3.97 (m, 2 H), 3.27-3.35 (m, 1H), 3.20-3.27 (m, 1 H), 2.80-2.95 (m, 1 H), 1.78-1.88 (m, 2 H), 1.64-1.78 (m, 2 H), 1.40-1.64 (m, 2 H). MS (EI): m/z=315 ([M+H]$^+$ of free base, 100%). EA for $C_{15}H_{17}F_3N_2O_2 \times HCl$: calcd: C 51.36, H 5.17, N 7.99, F 16.25; found C 51.19, H 4.89, N 7.91, F 16.06.

EXAMPLE 6

Synthesis of [3,4-Difluoro-2-(2-fluoro-4-iodo-phenylamino)-phenyl]-((S)-3-hydroxy-3-piperidin-2-yl-azetidin-1-yl)-methanone

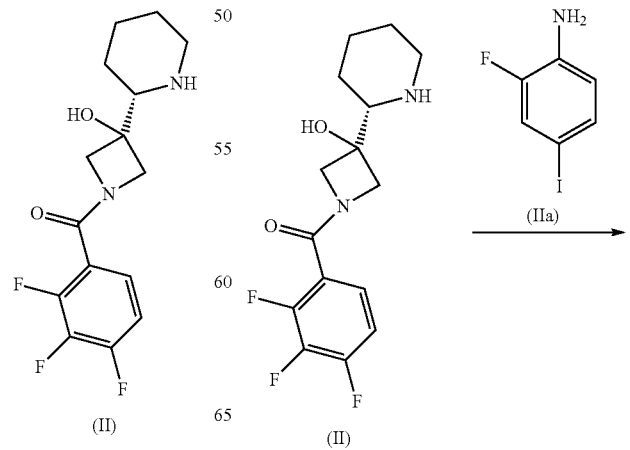

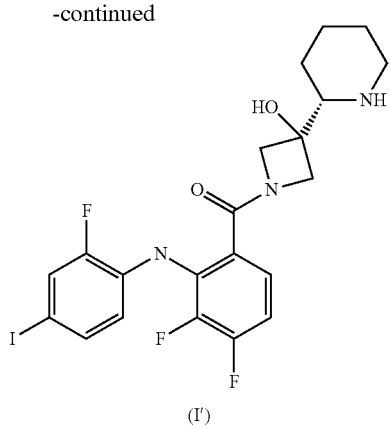

(I')

To a solution of ((S)-3-hydroxy-3-piperidin-2-yl-azetidin-1-yl)-(2,3,4-trifluoro-phenyl)-methanone hydrochloride (15.0 g, 42.8 mmol, 1.0 eq.) and 2-flouro-4-iodo-anilin (11.1 g, 47 mmol, 1.1 eq.) in THF (90 ml), a solution of LiHMDS in THF (149 g, 20.7% w/w, 184 mmol, 4.3 eq.) was dosed over 88 min at 20 to 30° C. Stirring was continued for 2 h. After complete conversion, the mixture was dosed to a mixture of sulfuric acid (12.0 g, 96%-w/w, 118 mmol, 2.75 eq.) in water (75 mL) over 25 min and kept stirring for 1 h. The layers were allowed to separate, and the organic phase was washed with a mixture of water (60 mL) and toluene (96 mL). The organic phase was concentrated under vacuum to a volume of approximately 150 mL. Toluene (250 mL) was added and residual THF was removed by distillation at 55° C. jacket temperature and at a pressure of 84 mbar while keeping the batch volume constant by continuous dosing of toluene (400 mL), resulting in slow precipitation of the product. The batch temperature was then lowered to 10° C. within 2 h, and the suspension was kept stirring overnight at 10° C. The product was filtered off, and the cake was rinsed with cold toluene (150 mL). Drying overnight under vacuum at 35° C. until weight constancy yielded the title compound (20.66 g) as a colorless product. HPLC purity: 99.7%-area. M.p (DSC): $T_{onset}$: 166.7° C., extrapolated peak: 168.2° C. (91.5 J/g). $^1$H NMR (600 MHz, CDCl$_3$): δ 8.28-8.48 (br, 1 H), 7.39 (dd, 1 H), 7.32 (ddd, 1 H), 7.09-7.14 (m, 1 H), 6.75-6.86 (br, 1 H), 6.60 (ddd, 1 H), 4.10 (d, 2 H), 4.05-4.20 (br, 1 H), 3.93-4.04 (br, 1 H), 3.09 (d, 1 H), 2.70 (d, 1 H), 2.56-2.67 (br, 1 H), 1.68-1.87 (m, 1 H), 1.50-1.64 (m, 2 H), 1.25-1.38 (m, 2 H), 1.07-1.24 (m, 1 H). MS (EI): m/z=532 ([M+H]$^+$, 100%). EA for $C_{21}H_{21}F_3IN_2O_3$: calcd: C 47.47, H 3.98, N 7.91, F 10.73; found C 47.68, H 4.00, N 7.66, F 10.80.

Other Embodiments

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

The invention claimed is:

1. A process for preparing a compound of formula I', comprising adding 4.3 molar equivalents of a strong base selected from the group consisting of the lithium, sodium, or potassium salt of bis(trimethylsilyl)amine as a solution in tetrahydrofuran to a mixture of 1.1 molar equivalents of a compound of formula II$_a$ and 1.0 molar equivalents of a compound of formula II as the hydrochloride in tetrahydrofuran:

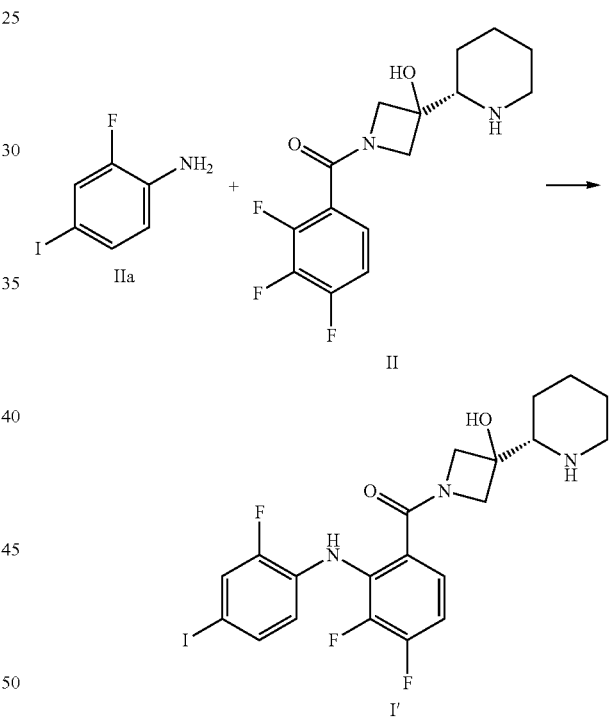

wherein the temperature of the process is 20 to 30° C.

2. The process of claim 1, wherein lithium bis(trimethylsilyl)amide is the strong base.

* * * * *

UNITED STATES PATENT AND TRADEMARK OFFICE
CERTIFICATE OF CORRECTION

PATENT NO. : 9,771,347 B2
APPLICATION NO. : 14/684826
DATED : September 26, 2017
INVENTOR(S) : Sriram Naganathan et al.

It is certified that error appears in the above-identified patent and that said Letters Patent is hereby corrected as shown below:

On the Title Page

Item (72), Line 9, add -- Neel Kumar Anand, San Mateo, CA (US) --

Signed and Sealed this
Seventeenth Day of September, 2019

Andrei Iancu
*Director of the United States Patent and Trademark Office*